(12) United States Patent
Zhao et al.

(10) Patent No.: US 12,180,175 B2
(45) Date of Patent: Dec. 31, 2024

(54) WATER-SOLUBLE YNAMIDE COUPLING REAGENT AND PREPARATION METHOD AND USE THEREOF

(71) Applicant: Xi'an Easy Peptide Biotechnology Co., Ltd., Shaanxi (CN)

(72) Inventors: Junfeng Zhao, Shaanxi (CN); Tao Liu, Shaanxi (CN)

(73) Assignee: Xi'an Easy Peptide Biotechnology Co., Ltd., Shaanxi (CN)

( * ) Notice: Subject to any disclaimer, the term of this patent is extended or adjusted under 35 U.S.C. 154(b) by 390 days.

(21) Appl. No.: 17/475,486

(22) Filed: Sep. 15, 2021

(65) Prior Publication Data

US 2022/0144793 A1    May 12, 2022

(30) Foreign Application Priority Data

Nov. 6, 2020    (CN) .......................... 202011229726.4

(51) Int. Cl.

| | | |
|---|---|---|
| *C07D 317/28* | (2006.01) | |
| *C07C 67/03* | (2006.01) | |
| *C07C 67/08* | (2006.01) | |
| *C07C 201/12* | (2006.01) | |
| *C07C 231/02* | (2006.01) | |
| *C07C 269/06* | (2006.01) | |
| *C07C 327/22* | (2006.01) | |
| *C07C 327/26* | (2006.01) | |
| *C07C 329/04* | (2006.01) | |
| *C07D 213/81* | (2006.01) | |
| *C07D 213/83* | (2006.01) | |
| *C07D 215/48* | (2006.01) | |
| *C07D 295/185* | (2006.01) | |
| *C07D 333/70* | (2006.01) | |
| *C07J 1/00* | (2006.01) | |
| *C07K 5/06* | (2006.01) | |

(52) U.S. Cl.
CPC ............ *C07D 317/28* (2013.01); *C07C 67/03* (2013.01); *C07C 231/02* (2013.01); *C07C 329/04* (2013.01)

(58) Field of Classification Search
CPC ................ C07D 317/28; C07D 213/81; C07D 213/83; C07D 215/48; C07D 295/185; C07D 333/70; C07C 67/03; C07C 231/02; C07C 329/04; C07C 67/08; C07C 201/12; C07C 269/06; C07C 327/22; C07C 327/26; C07C 233/22; C07C 271/22; C07C 205/57; C07C 233/11; C07C 69/618; C07J 1/0059; C07K 5/06026; C07K 5/06034; C07K 5/0606
See application file for complete search history.

(56) References Cited

PUBLICATIONS

Yang, M., X. Wang, and J. Zhao, "Ynamide-Mediated Macrolactonization", ACS Catal. (2020), 10, 5230-5235. (Year: 2020).*
Hu, L. and J. Zhao, "Ynamide: A New Coupling Reagent for Amide and Peptide Synthesis", New York—Synlett (2017), 28, pp. 1663-1670. (Year: 2017).*

* cited by examiner

*Primary Examiner* — Amanda L. Aguirre
*Assistant Examiner* — Sagar Patel
(74) *Attorney, Agent, or Firm* — Sughrue Mion, PLLC

(57) ABSTRACT

The present disclosure discloses a water-soluble ynamide coupling reagent and a method for using the water-soluble ynamide coupling reagent in the synthesis of amide, polypeptide, ester and thioester compound. The ynamide coupling reagent has the structure represented by the following formula (I):

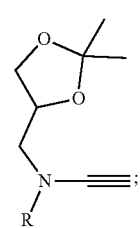

(I)

and in the formula (I), R is one selected from the group consisting of methylsulfonyl, benzenesulfonyl, p-toluenesulfonyl, trifluoroacetyl and other electron withdrawing groups.

9 Claims, No Drawings

WATER-SOLUBLE YNAMIDE COUPLING REAGENT AND PREPARATION METHOD AND USE THEREOF

CROSS REFERENCE TO RELATED APPLICATION

This patent application claims the benefit and priority of Chinese Patent Application No. 202011229726.4 filed on Nov. 6, 2020, the disclosure of which is incorporated by reference herein in its entirety as part of the present application.

TECHNICAL FIELD

The present disclosure relates to a ynamide coupling reagent and use thereof, and in particular to a water-soluble ynamide coupling reagent whose by-product could be removed by washing with water, and a preparation method and use thereof, belonging to the technical field of organic synthetic chemistry.

BACKGROUND ART

Amide bonds widely exist in various functional materials, medicines, pesticides and various fine chemicals, and they are a very important type of functional group in organic chemistry. Amide bonds are the basic structural units of proteins. Peptides and proteins are biological macromolecules with important functional activities that are connected by natural amino acids through amide bonds in a specific order, and play an important role in regulating various life activities. The traditional method for forming amide bond or peptide bond is mainly performed by activating carboxylic acid to form active intermediates such as acyl chloride, acid anhydride, activated ester and acyl azide by activating reagents or coupling reagents, and the active intermediates subject to a nucleophilic substitution reaction with amine to form amide or polypeptide. Among various methods for forming peptide bonds, the coupling reagent method is currently the most widely used method in peptide synthesis.

N,N'-dicyclohexylcarbodiimide (DCC) is the first carbodiimide type coupling reagent developed by Sheehan in 1955 (J. Am. Chem. Soc. 1955, 77, 1067-1068), and it is still one of the most commonly used coupling reagents. However, the by-product N,N'-dicyclohexylurea (DCU) produced by the reaction has poor solubility in most solvents, and it is difficult to completely remove it from the target product even by centrifugation and column chromatography. In order to simplify the post-treatment of the reaction, more soluble carbodiimide coupling reagents, such as N,N'-diisopropylcarbodiimide (DIC) (J. Chem. Soc., Chem. Commun. 1981, 543-545), and carbodiimide coupling reagents whose by-product could be removed by washing with water, such as 1-(3-dimethylaminopropyl)-3-ethylcarbodiimide hydrochloride (EDCI) (J. Org. Chem. 1961, 26, 2525-2528), 1,3-bis (2,2-dimethyl-1,3-dioxolane-4-ylmethyl)carbodiimide (BDDC) (J. Org. Chem. 1994, 59, 7503-7507) are developed. However, the carbodiimide coupling reagent usually cause serious racemization during the polypeptide condensation. Therefore, racemization suppressors are developed for use in conjunction with the carbodiimide coupling reagents. The more commonly used racemization suppressors are N-hydroxysuccinimide (HOSu) (J. Am. Chem. Soc. 1964, 86, 1839-1842), 1-hydroxybenzotriazole (HOBt) (Chem. Ber. 1970, 103, 788-798), N-hydroxy-7-azabenzotriazide (HOAt) (J. Am. Chem. Soc. 1993, 115, 4397-4398) and the like. For ease of use, many scientists have designed the functions of racemization suppressors and coupling reagents on the same molecules, such as phosphate salt coupling reagents, urea/ammonium salt coupling reagents, and imine salt coupling reagents. Among them, the coupling reagents, such as 1H-benzotriazol-1-yloxytripyrrolidinyl hexafluorophosphate (PyBOP) (Tetrahedron Lett. 1990, 31, 205-208), benzotriazole-N,N,N',N'-tetramethylurea hexafluorophosphate (HBTU) (Tetrahedron Lett. 1978, 19, 1269-1272) and N,N,N',N'-tetramethyl-O-(7-azabenzotriazole-1-yl)hexafluorourea phosphate (HATU) (Tetrahedron Lett. 1994, 35, 2279-2282) have the advantages such as high condensation efficiency and small degree of racemization, and have been widely used in the field of peptide synthesis. So far, many coupling reagents have been developed. However, most commonly used coupling reagents require the addition of equivalent or excess alkalis and racemization suppressors to achieve better reaction effects. These additional additives greatly reduce the atom economy of peptide synthesis, not only increase the cost of peptide synthesis, but also put great pressure on environmental protection.

In 2016, Junfeng Zhao's research group designed and developed a novel type of ynamide coupling reagent for the synthesis of amide bond and peptide bond (J. Am. Chem. Soc. 2016, 138, 13135-13138). This novel type of coupling reagent has the advantages such as easy preparation, good stability, small molecular weight, mild reaction conditions, and no additives during use. More importantly, the α-chiral acid does not racemize during the condensation process, which greatly improves the purity and yield of the product. However, the aminolysis reaction promoted by the existing ynamide coupling reagents must separate and purify the product by column chromatography, thereby resulting in higher costs.

SUMMARY

The present disclosure improves the structure of ynamide on the basis of the prior art, and develops a ynamide coupling reagent whose by-product could be removed by washing with water. The novel water-soluble ynamide coupling reagent not only has the advantages such as easy preparation, no additional additives, no racemization, and a wide application range of substrate, but also making the by-product dissolve in water by the hydrolysis of a weak acid after the reaction completed. The by-product could be removed by washing with water, which simplifies the post-treatment process of the product.

According to the first embodiment of the present disclosure, a water-soluble ynamide coupling reagent is provided.

A water-soluble ynamide coupling reagent, wherein the ynamide coupling reagent has the structure represented by the following formula (I):

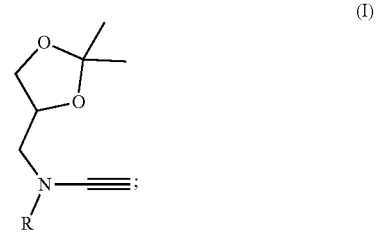

and
wherein, R is one selected from the group consisting of methylsulfonyl, benzenesulfonyl, p-toluenesulfonyl, trifluoroacetyl and other electron withdrawing groups.

According to the second embodiment of the present disclosure, a method for preparing the water-soluble ynamide coupling reagent having the structure represented by formula (I) is provided, comprising:

1) mixing N-(2,2-dimethyl-1,3-dioxolane-4-ylmethyl) amide having the structure represented by formula (II) and ethylene dichloride in solvent I to obtain a mixture;

2) adding an alkali into the mixture obtained in step 1), and subjecting the resulting mixture to a reaction, and separating to obtain the water-soluble ynamide coupling reagent having the structure represented by formula (I); the specific reaction is performed as follow:

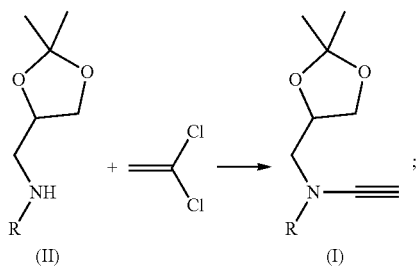

and
wherein, R is one selected from the group consisting of methylsulfonyl and p-toluenesulfonyl.

In some embodiments, in step 1), the solvent I is an organic solvent, and preferably, the solvent I is at least one selected from the group consisting of dimethyl sulfoxide, N,N-dimethylformamide, N,N-dimethylacetamide and N-methylpyrrolidone.

In some embodiments, a molar ratio of N-(2,2-dimethyl-1,3-dioxolane-4-ylmethyl) amide having the structure represented by formula (II) to ethylene dichloride is in a range of 1:(0.8-5), preferably 1:(1-3), and more preferably 1:(1.1-2).

In some embodiments, in step 2), the alkali is at least one selected from the group consisting of NaH, CaH$_2$, t-BuONa, KOH, NaOH, EtONa, EtOLi, Cs$_2$CO$_3$, K$_2$CO$_3$, Na$_2$CO$_3$, Ca(OH)$_2$, LiOH and DBU.

In some embodiments, in step 2), the reaction is performed at a temperature of 15-100° C., preferably 20-90° C., and more preferably 25-80° C.; and the reaction is performed for 0.2-48 h, preferably 0.5-36 h, and more preferably 1-24 h.

In some embodiments, in step 2), the separating is performed by filtration, centrifugation or column chromatography.

In some embodiments, in step 2), a molar ratio of the alkali to N-(2,2-dimethyl-1,3-dioxolane-4-ylmethyl) amide having the structure represented by formula (II) is in a range of (1-10):1, preferably (2-8):1, and more preferably (3-6):1.

According to the third embodiment of the present disclosure, use of the water-soluble ynamide coupling reagent is provided.

Use of the water-soluble ynamide coupling reagent, wherein the water-soluble ynamide coupling reagent having the structure represented by formula (I) is used in the synthesis of amide, polypeptide, an ester compound or a thioester compound.

In some embodiments, the method for using the water-soluble ynamide coupling reagent to synthesize an ester compound or a thioester compound is performed as follows:

1a) subjecting a carboxylic acid compound and the water-soluble ynamide coupling reagent having the general molecular formula (I) to a reaction in solvent II to obtain a compound having the structure represented by formula (III); the specific reaction is performed as follow:

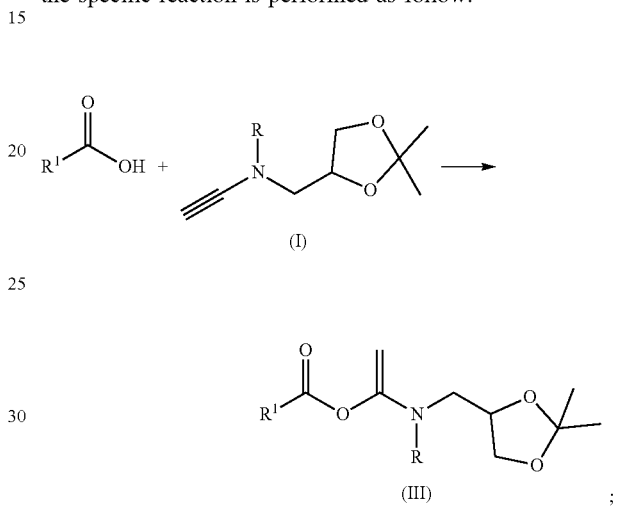

2a) after the reaction in step 1a) completed, dissolving the compound having the structure represented by formula (III) obtained in solvent III, adding one selected from the group consisting of alcohol compound, phenol compound, thiol compound or thiophenol compound thereto, and adding a catalyst thereto, stirring for a reaction to obtain a mixture containing an ester compound or a thioester compound, and a by-product; the specific reaction is performed as follow:

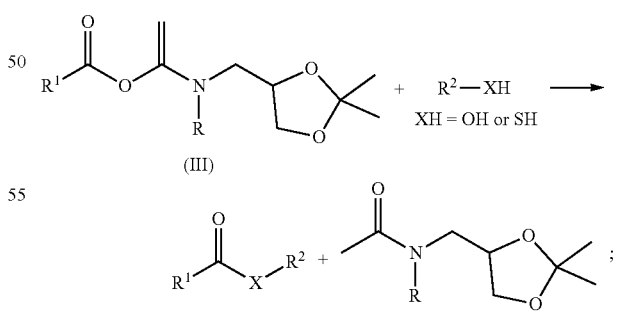

3a) adding a dilute acid aqueous solution into the mixture containing an ester compound or a thioester compound obtained in step 2a), hydrolyzing the unreacted coupling reagent and the by-product produced in the reaction, and separating to obtain the target ester compound or thioester compound; the reaction is performed as follow:

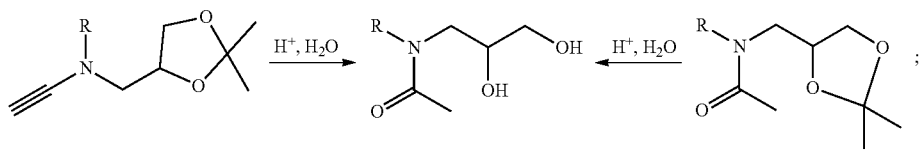

and in the formula, $R^1$ is one selected from the group consisting of alkyl, cycloalkyl, alkenyl, alkynyl, aryl, heterocyclic, heterocyclic aryl, protected α-aminoalkyl, protected β-aminoalkyl, protected polypeptide chain alkyl, and R is one selected from the group consisting of methylsulfonyl, benzenesulfonyl, p-toluenesulfonyl, trifluoroacetyl and other electron withdrawing groups, and $R^2$ is one selected from the group consisting of aliphatic substituent group and aromatic substituent group.

In some embodiments, in step 1a), the carboxylic acid compound is an organic acid formed by the association of a hydrocarbon group and a carboxyl group.

In some embodiments, in step 1a), the carboxylic acid compound is preferably at least one selected from the group consisting of fatty acid, aromatic acid, heterocyclic acid, acetylenic acid, olefine acid, α-amino acid and β-amino acid, and the carboxylic acid compound is more preferably one selected from the group consisting of formic acid, acetic acid, phenylacetic acid, lithocholic acid and other aliphatic carboxylic acids, proprionic acid, phenylpropionic acid, cinnamic acid, acrylic acid and other unsaturated acids, benzoic acid, p-toluic acid, p-chlorobenzoic acid, pyridine-2-formic acid, furan-2-formic acid and other aromatic acids, benzyloxycarbonyl-protected α-amino acid, tert-butoxycarbonyl-protected α-amino acid, fluorenylmethyloxycarbonyl-protected α-amino acid, acetyl-protected α-amino acid and polypeptide carboxylic acid.

In some embodiments, in step 1a), a molar ratio of the carboxylic acid compound to the water-soluble ynamide coupling reagent having the general molecular formula (I) is in a range of 1:(1-5), preferably 1:(1.1-4), and more preferably 1:(1.2-3).

In some embodiments, in step 1a), the solvent II is any one selected from the group consisting of dichloromethane, water, chloroform, 1,2-dichloroethane, or the solvent II is a mixture of water and dimethylsulfoxide, or a mixture of water and N,N-dimethylformamide.

In some embodiments, in step 2a), the alcohol compound, the phenol compound, the thiol compound and the thiophenol compound are organic compounds with the functional group of —OH or —SH.

In some embodiments, in step 2a), the alcohol compound, the phenol compound, the thiol compound and the thiophenol compound are preferably organic compounds with the functional group of —OH or —SH in aliphatic alcohol and aromatic alcohol; the alcohol compound, the phenol compound, the thiol compound and the thiophenol compound are more preferably any one selected from the group consisting of ethanol, trifluoroethanol, propanol, butanol, isopropyl alcohol and other aliphatic primary alcohols and secondary alcohols, phenol, estrone, p-methoxyphenol, p-chlorophenol, p-nitrophenol and other substituted phenols, ethanethiol, 1-hexanethiol, cyclohexanethiol, 2-methyl-2-propanethiol and other aliphatic thiols, 4-mercaptobenzoic acid, p-methylthiophenol, p-chlorothiophenol, p-bromothiophenol and other substituted thiophenols, amino-protected cysteine ester and sulfhydryl group of polypeptide side chain.

In some embodiments, in step 2a), a molar ratio of the alcohol compound, the phenol compound, the thiol compound and the thiophenol compound and the carboxylic acid compound is in a range of 1:(1-20), preferably 1:(1.5-15), and more preferably 1:(2-10).

In some embodiments, in step 2a), the solvent III is at least one selected from the group consisting of water, acetonitrile, dimethyl sulfoxide, N,N-dimethylformamide, N,N-dimethylacetamide, N-methylpyrrolidone, a mixture of acetonitrile and water, a mixture of water and dimethylsulfoxide, and a mixture of water and N,N-dimethylformamide.

In some embodiments, in step 2a), the catalyst is triethylamine or N,N-diisopropylethylamine.

In some embodiments, in step 2a), a molar ratio of the catalyst to the carboxylic acid compound is in a range of (0.01-10):1, preferably (0.02-5):1, and more preferably (0.03-1):1.

In some embodiments, in step 3a), the dilute acid is one selected from the group consisting of dilute sulfuric acid, dilute hydrochloric acid, phosphoric acid, acetic acid and citric acid; and the concentration of the dilute acid is in a range of 0.01-5 mol/L, preferably 0.5-2 mol/L, and more preferably 0.1-1 mol/L.

In some embodiments, the step 1a) is performed as follows: adding a carboxylic acid compound, the water-soluble ynamide coupling reagent having the general molecular formula (I) and solvent II into a reactor for mixing, and stirring for a reaction at a temperature of 0-60° C. (preferably 5-50° C.), after the reaction completed, removing the solvent II to obtain a compound having the structure represented by formula (III).

In some embodiments, the step 2a) is performed as follows: after the reaction in step 1a) completed, dissolving the compound having the structure represented by formula (III) obtained in step 1a) into solvent III, adding one selected from the group consisting of alcohol compound, phenol compound, thiol compound and thiophenol compound thereto, and then adding a catalyst thereto, and stirring, and then stirring for a reaction at a temperature of 0-60° C. (preferably 5-50° C.) to obtain a mixture containing an ester compound or a thioester compound and a by-product.

In some embodiments, the step 3a) is performed as follows: optionally adding a diluent into the mixture containing an ester compound or a thioester compound obtained in step 2a) for dilution (preferably, the diluent is dichloromethane or ethyl acetate), and then adding a diluted acid aqueous solution for washing, hydrolyzing the unreacted coupling reagent and the by-product produced in the reaction to precipitate a product, filtering the product, and washing with water to obtain the target ester compound or thioester compound.

In some embodiments, the method for using the water-soluble ynamide coupling reagent to synthesize an amide compound or a polypeptide compound is performed as follows:

1b) subjecting a carboxylic acid compound and the water-soluble ynamide coupling reagent having the general molecular formula (I) to a reaction in solvent II to obtain a compound having the structure represented by the formula (IV); the specific reaction is performed as follow:

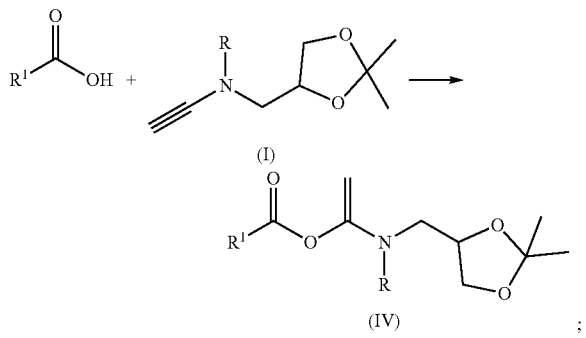

2b) after the reaction in step 1b) completed, adding an amine compound into the obtained compound having the structure represented by formula (IV), and stirring for a reaction to obtain a mixture containing an amide compound or a polypeptide compound and a by-product; the specific reaction is performed as follow:

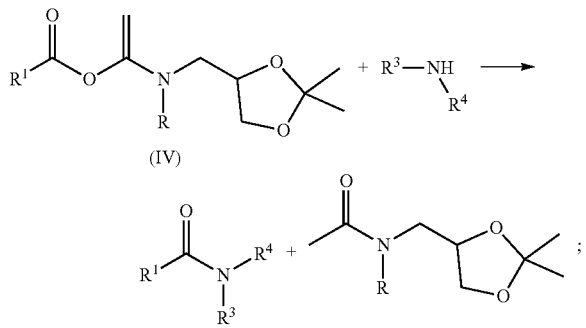

3b) adding a diluent and a diluted acid aqueous solution into the mixture containing an amide compound or a polypeptide compound and a by-product obtained in step 2b), hydrolyzing the unreacted coupling reagent and the by-product produced in the reaction, and separating to obtain the target amide compound or polypeptide compound; the reaction is performed as follow:

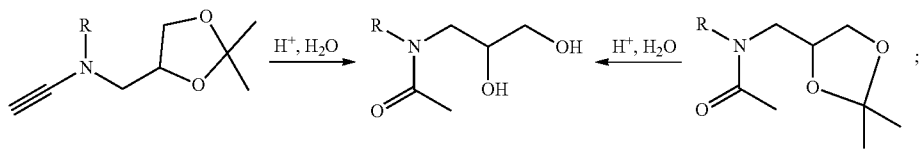

and in the formula, $R^1$ is one selected from the group consisting of alkyl, cycloalkyl, alkenyl, alkynyl, aryl, heterocyclic, heterocyclic aryl, protected α-aminoalkyl, protected β-aminoalkyl and protected polypeptide chain alkyl; R is one selected from the group consisting of methylsulfonyl, benzenesulfonyl, p-toluenesulfonyl, trifluoroacetyl and other electron withdrawing groups; $R^3$ and $R^4$ are one selected from the group consisting of selected from aliphatic substituent group and aromatic substituent group.

In some embodiments, in step 1b), the carboxylic acid compound is an organic acid formed by the association of a hydrocarbon group and a carboxyl group.

In some embodiments, in step 1b), the carboxylic acid compound is preferably any one selected from the group consisting of fatty acid, aromatic acid, heterocyclic acid, acetylenic acid, olefine acid, α-amino acid, β-amino acid; and the carboxylic acid compound is more preferably formic acid, acetic acid, phenylacetic acid, lithocholic acid and other aliphatic carboxylic acids, propiolic acid, phenylpropynoic acid, cinnamic acid, acrylic acid and other unsaturated acids, benzoic acid, p-toluic acid, p-chlorobenzoic acid, pyridine-2-formic acid, furan-2-formic acid and other aromatic acids, benzyloxycarbonyl-protected α-amino acid, tert-butoxycarbonyl-protected α-amino acid, fluorenylmethyloxycarbonyl-protected α-amino acid, acetyl-protected α-amino acid and polypeptide carboxylic acid.

In some embodiments, in step 1b), a molar ratio of the carboxylic acid compound to the water-soluble ynamide coupling reagent having the general molecular formula (I) is in a range of 1:(1-5), preferably 1:(1.1-4), and more preferably 1:(1.2-3).

In some embodiments, in step 1b), the solvent II is an organic solvent.

In some embodiments, in step 1b), the solvent II is preferably any one selected from the group consisting of dichloromethane, water, chloroform, 1,2-dichloroethane, or the solvent II is a mixture of water and dimethylsulfoxide, or a mixture of water and N,N-dimethylformamide.

In some embodiments, in step 2b), the amine compound is a primary amine or a secondary amine, and the amine compound is preferably any one selected from the group consisting of primary aliphatic amine, secondary aliphatic amine, aromatic amine, α-amino acid methyl ester, α-amino acid ethyl ester, α-amino acid tert-butyl ester, α-amino acid benzyl ester, β-amino acid methyl ester, β-amino acid ethyl ester, β-amino acid tert-butyl ester and β-amino acid benzyl ester.

In some embodiments, in step 2b), a molar ratio of the carboxylic acid compound to the amine compound is in a range of 1:(1-5), preferably 1:(1.1-4), and more preferably 1:(1.2-3).

In some embodiments, in step 3b), the dilute acid is any one selected from the group consisting of dilute sulfuric acid, dilute hydrochloric acid, phosphoric acid, acetic acid and citric acid.

In some embodiments, in step 3b), a concentration of the dilute acid is in a range of 0.01-5 mol/L, preferably 0.5-2 mol/L, and more preferably 0.1-1 mol/L.

In some embodiments, the step 1b) is performed as follows: adding a carboxylic acid compound, the water-soluble ynamide coupling reagent having the general molecular formula (I) and solvent II into a reactor for mixing, and stirring for a reaction at a temperature of 0-60°

C. (preferably 5-50° C.) to obtain a compound having a structure represented by formula (IV).

In some embodiments, the step 2b) is performed as follows: after the reaction in step 1b) completed, adding an amine compound into the compound having the structure represented by formula (IV) obtained in step 1b), and then stirring for a reaction at a temperature of 0-60° C. (preferably 5-50° C.) to obtain a mixture containing an amide compound or a polypeptide compound and a by-product.

In some embodiments, the step 3b) is performed as follows: adding a diluent (the diluent preferably is dichloromethane or ethyl acetate) into the mixture containing an amide compound or a polypeptide compound obtained in step 2b); and then adding a dilute acid aqueous solution for washing, hydrolyzing the unreacted coupling reagent and the by-product obtained in the reaction to precipitate a product, filtering the product, and washing with water to obtain the target amide compound or polypeptide compound.

In some embodiments, the step 3b) is performed as follows: removing the solvent in the mixture containing an amide compound or a polypeptide compound obtained in step 2b), adding solvent IV (the solvent IV preferably is one selected from the group consisting of methanol, ethanol, isopropanol and acetonitrile), and then adding a dilute acid for washing, hydrolyzing the unreacted coupling reagent and the by-product obtained in the reaction to precipitate a product, filtering the product, and washing with water to obtain the target amide compound or polypeptide compound.

In the present disclosure, N-(2,2-dimethyl-1,3-dioxolane-4-ylmethyl)amide having the structure represented by formula (II) is shown as follows: N-(2,2-dimethyl-1,3-dioxolane-4-ylmethyl)methanesulfonamide (the structural formula is shown as Preparation Example 1), N-(2,2-dimethyl-1,3-dioxolane-4-ylmethyl)benzenesulfonamide (the structural formula is shown as Preparation Example 2), N-(2,2-dimethyl-1,3-dioxolane-4-ylmethyl)p-toluenesulfonamide (the structural formula is shown as Preparation Example 3) or N-(2,2-dimethyl-1,3-dioxolane-4-ylmethyl)trifluoroacetamide (the structural formula is shown as Preparation Example 4).

In the present disclosure, N-(2,2-dimethyl-1,3-dioxolane-4-ylmethyl)methanesulfonamide (the structural formula is shown as Preparation Example 1) is prepared by the following method:

Under ice bath conditions, (2,2-dimethyl-[1,3]-dioxolane-4-yl)-methylamine and 3 times the amount of triethylamine are mixed in a dichloromethane solution, and stirred, and methanesulfonyl chloride equivalent to (2,2-dimethyl-[1,3]-dioxolane-4-yl)-methylamine is slowly dropwise added thereto for a reaction. The reaction is detected by TCL (thin-layer chromatography). After the reaction completed, water is added into the reaction product, to obtain an aqueous phase and an organic phase. The aqueous phase is extracted twice with dichloromethane. The organic phase is combined, and washed with saturated brine, and separated, to obtain a separated organic phase. The separated organic phase is dried with anhydrous sodium sulfate and concentrated, to obtain N-(2,2-dimethyl-1,3)-dioxolane-4-ylmethyl)methanesulfonamide.

In the present disclosure, N-(2,2-dimethyl-1,3-dioxolane-4-ylmethyl)benzenesulfonamide (the structural formula is shown as Preparation Example 2) is prepared by the following method:

Under ice bath conditions, (2,2-dimethyl-[1,3]-dioxolane-4-yl)-methylamine and 3 times the amount of triethylamine are mixed in a dichloromethane solution, and stirred, and benzenesulfonyl chloride equivalent to (2,2-dimethyl-[1,3]-dioxolane-4-yl)-methylamine is slowly dropwise added thereto for a reaction. The reaction is detected by TCL. After the reaction completed, water is added into the reaction product, to obtain an aqueous phase and an organic phase. The aqueous phase is extracted twice with dichloromethane. The organic phase is combined, and washed with saturated brine, and separated, to obtain a separated organic phase. The separated organic phase is dried with anhydrous sodium sulfate and concentrated, to obtain N-(2,2-dimethyl-1,3)-dioxolane-4-ylmethyl)benzenesulfonamide.

In the present disclosure, N-(2,2-dimethyl-1,3-dioxolane-4-ylmethyl)p-toluenesulfonamide (the structural formula is shown as Preparation Example 3) is prepared by the following method:

Under ice bath conditions, (2,2-dimethyl-[1,3]-dioxolane-4-yl)-methylamine and 3 times the amount of triethylamine are mixed in a dichloromethane solution, and stirred, and p-toluenesulfonyl chloride equivalent to (2,2-dimethyl-[1,3]-dioxolane-4-yl)-methylamine is slowly dropwise added thereto for a reaction. The reaction is detected by TCL. After the reaction completed, water is added into the reaction product, to obtain an aqueous phase and an organic phase. The aqueous phase is extracted twice with dichloromethane. The organic phase is combined, and washed with saturated brine, and separated, to obtain a separated organic phase. The separated organic phase is dried with anhydrous sodium sulfate and concentrated, to obtain N-(2,2-dimethyl-1,3)-dioxolane-4-ylmethyl)p-toluenesulfonamide.

In the present disclosure, N-(2,2-dimethyl-1,3-dioxolane-4-ylmethyl)trifluoroacetamide (the structural formula is shown as Preparation Example 4) is prepared by the following method:

Under ice bath conditions, (2,2-dimethyl-[1,3]-dioxolane-4-yl)-methylamine and 3 times the amount of triethylamine are mixed in a dichloromethane solution, and stirred, and trifluoroacetyl chloride equivalent to (2,2-dimethyl-[1,3]-dioxolane-4-yl)-methylamine is slowly dropwise added thereto for a reaction. The reaction is detected by TCL. After the reaction completed, water is added into the reaction product, to obtain an aqueous phase and an organic phase. The aqueous phase is extracted twice with dichloromethane. The organic phase is combined, and washed with saturated brine, and separated, to obtain a separated organic phase. The separated organic phase is dried with anhydrous sodium sulfate and concentrated, to obtain N-(2,2-dimethyl-1,3)-dioxolane-4-ylmethyl)trifluoroacetamide In the present disclosure, the reaction which could generate the α-acyloxyenamide compound in the first step basically could not occur in the solvents, such as N,N-dimethylformamide, N,N-dimethylacetamide, 1,4-dioxane and tetrahydrofuran however, it could occur in acetone, acetonitrile and methanol, nevertheless, it has a slower reaction rate. The reaction has the best effect in a halogenated hydrocarbon solvents, such as dichloromethane, 1,2-dichloromethane and chloroform, and it is completed in 1-2 h at room temperature, and the product yield could reach almost 100%.

In the present disclosure, the α-acyloxyenamide compound is an activated ester, and it could react smoothly with primary or secondary amine at room temperature to prepare amide and polypeptide. The addition reaction of carboxylic acid with ynamide and the aminolysis reaction of carboxylic acid with an α-acyloxyenamide compound could be carried out step by step, or could be realized by a "one-pot method".

In the present disclosure, a ketal structure (2,2-dimethyl-1,3-dioxolane-4-yl) is introduced to the ynamide coupling reagent, and it could be hydrolyzed under weakly acidic conditions to produce two hydroxyl groups, greatly increasing the water solubility of the ynamide coupling reagent and the by-product. Therefore, after the reaction completed, the by-product and the redundant ynamide coupling reagent could be hydrolyzed by a weak acid, thereby dissolving in water, and could be removed by washing with water, thereby realizing the simple separation of the product, avoiding the operations of column chromatography, such as separation and purification. The water-soluble ynamide coupling reagent prepared by the present disclosure is used to prepare compounds such as amide, polypeptide, ester and thioester, and has a purity of 95-99%. Among them, the optical purity of the chiral compounds of amide, polypeptide, ester and thioester prepared by the present disclosure is more than 99%.

In addition, there is no need for additional additives and alkalis during the use of the coupling reagent. The synthesis of amide compound and polypeptide compound, ester compound and thioester compound could be realized by the "one-pot method" under mild conditions. Especially in the reaction of a natural α-amino acid with other chiral acids, it is very important to maintain the chiral purity of the product. The water-soluble ynamide coupling reagent could effectively control the racemization of the chiral acid during the synthesis process. Therefore, after the reaction, the separation of the product and the by-product could be realized only by washing with a weak acid, and the product with very high purity could be obtained without the need for the operations of column chromatography, such as separation and purification, making the synthesis of amide compound and polypeptide compound, ester compound and thioester compound more concisely and conveniently. The method has little impact on the environment, and is very green and environmental protection.

Compared with the prior art, the present disclosure has the following beneficial effects:

1. Compared with the traditional coupling reagents, such as DCC, PyBOP and HBTU, the novel water-soluble ynamide coupling reagent in the present disclosure has better performance, and could be used to prepare amide, polypeptide, ester and thioester compounds efficiently and conveniently.

2. After the reaction complete, the by-product could be dissolved in water by the hydrolysis of a weak acid, and could be removed by washing with water, which could simplify the post-treatment process of the product.

3. The novel water-soluble ynamide coupling reagent in the present disclosure does not require additional additives during the process of promoting the formation of amide bond and ester bond, which improves the atom economy of the reaction.

4. The novel water-soluble ynamide coupling reagent in the present disclosure is used to prepare amide, polypeptide, ester and thioester compounds, and water is used to purify the products in the post-treatment process, which avoids the use of excessive organic solvent, and has little impact on the environment, and is very green and environmental protection.

DETAILED DESCRIPTION OF THE EMBODIMENTS

The technical solutions of the present disclosure will be illustrated below with reference to the examples, and the protection scope of the present disclosure includes, but is not limited to the following examples.

Preparation Example 1

Preparation of N-(2,2-dimethyl-1,3-dioxolane-4-ylmethyl)methanesulfonamide

Under ice bath conditions, 5 mmol of (2,2-dimethyl[1,3]-dioxolane-4-yl)-methylamine and 15 mmol of triethylamine were mixed in a dichloromethane solution, and stirred, and then 5 mol of methylsulfonyl chloride was slowly dropwise added thereto for a reaction. The reaction was detected by TCL. After the reaction completed, water was added into the reaction product, obtaining an aqueous phase and an organic phase. The aqueous phase was extracted twice with dichloromethane. The organic phase was combined, and washed once with saturated brine, and separated, obtaining a separated organic phase. The separated organic phase was dried with anhydrous sodium sulfate and concentrated, obtaining N-(2,2-dimethyl-1,3-dioxolane-4-ylmethyl)methanesulfonamide. The product is a light yellow liquid with a yield of 98%. The structural formula, and the experimental data of NMR and mass spectrometry of the product are shown as follows:

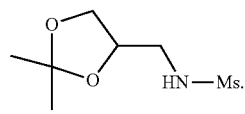

$^1$H NMR (400 MHz, CDCl$_3$) δ 4.73 (s, 1H), 4.28 (qd, J=6.3, 3.9 Hz, 1H), 4.07 (dd, J=8.5, 6.5 Hz, 1H), 3.75 (dd, J=8.5, 6.0 Hz, 1H), 3.34 (ddd, J=13.3, 6.7, 3.8 Hz, 1H), 3.23-3.16 (m, 1H), 3.00 (s, 3H), 1.44 (s, 3H), 1.35 (s, 3H).

$^{13}$C NMR (100 MHz, CDCl$_3$) δ=109.9, 74.5, 66.6, 45.6, 40.7, 26.9, 25.3.

HRMS (ESI) m/z calcd. for C$_7$H$_{16}$NO$_4$S [M+H]$^+$: 210.0795. found: 210.0800.

Preparation Example 2

Preparation of N-(2,2-dimethyl-1,3-dioxolane-4-ylmethyl)benzenesulfonamide

Under ice bath conditions, 5 mmol of (2,2-dimethyl[1,3]-dioxolane-4-yl)-methylamine and 15 mmol of triethylamine were mixed in a dichloromethane solution, and stirred, and then 5 mol of benzenesulfonyl chloride was slowly dropwise added thereto for a reaction. The reaction was detected by TCL. After the reaction completed, water was added into the reaction product, obtaining an aqueous phase and an organic phase. The aqueous phase was extracted twice with dichloromethane. The organic phase was combined, and washed once with saturated brine, and separated, obtaining a separated organic phase. The separated organic phase was dried with anhydrous sodium sulfate and concentrated, obtaining N-(2,2-dimethyl-1,3-dioxolane-4-ylmethyl)benzenesulfonamide. The product is a white solid with a yield of 95%. The structural formula, and the experimental data of NMR and mass spectrometry of the product are shown as follows:

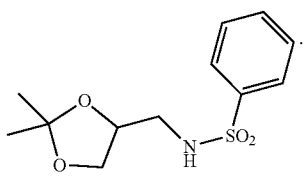 [SMILES: CC1(C)OCC(CNS(=O)(=O)c2ccccc2)O1]

¹H NMR (400 MHz, CDCl₃) δ 7.90-7.83 (m, 2H), 7.80 (s, 1H), 7.66-7.56 (m, 3H), 4.05 (p, J=7.0 Hz, 1H), 3.96 (dd, J=11.4, 7.0 Hz, 1H), 3.71 (dd, J=11.4, 6.9 Hz, 1H), 3.59 (dd, J=12.4, 7.0 Hz, 1H), 3.39 (dd, J=12.4, 7.0 Hz, 1H), 1.39 (s, 3H), 1.34 (s, 3H).

¹³C NMR (100 MHz, CDCl₃) δ 140.0, 133.8, 129.5, 128.2, 109.4, 74.6, 67.0, 46.7, 25.5.

HRMS (ESI) m/z calcd. for $C_{12}H_{18}NO_4S$ [M+H]⁺: 272.0951. found: 272.0959.

Preparation Example 3

Preparation of N-(2,2-dimethyl-1,3-dioxolane-4-ylmethyl)p-toluenesulfonamide in the Present Disclosure Under ice bath conditions, 5 mmol of (2,2-dimethyl-[1,3]-dioxolane-4-yl)-methylamine and 15 mmol of triethylamine were mixed in a dichloromethane solution, and stirred, and then 5 mol of p-toluenesulfonyl chloride was slowly dropwise added thereto for a reaction. The reaction was detected by TCL. After the reaction completed, water was added into the reaction product, obtaining an aqueous phase and an organic phase. The aqueous phase was extracted twice with dichloromethane. The organic phase was combined, and washed once with saturated brine, and separated, obtaining a separated organic phase. The separated organic phase was dried with anhydrous sodium sulfate and concentrated, obtaining N-(2,2-dimethyl-1,3-dioxolane-4-ylmethyl)p-toluenesulfonamide. The product is a white solid with a yield of 97%. The structural formula, and the experimental data of NMR and mass spectrometry of the product are shown as follows:

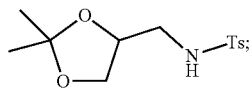

¹H NMR (400 MHz, CDCl₃) δ 7.75 (d, J=8.3 Hz, 2H), 7.31 (d, J=8.1 Hz, 2H), 4.94-4.77 (m, 1H), 4.22-4.14 (m, 1H), 3.99 (dd, J=8.4, 6.4 Hz, 1H), 3.68 (dd, J=8.5, 6.0 Hz, 1H), 3.13 (dddd, J=12.8, 7.0, 4.1, 1.6 Hz, 1H), 3.00-2.93 (m, 1H), 2.43 (s, 3H), 1.35 (s, 3H), 1.30 (s, 3H).

¹³C NMR (100 MHz, CDCl₃) δ 143.7, 136.9, 129.9, 127.2, 109.8, 74.1, 66.7, 45.4, 26.9, 25.3, 21.6.

HRMS (ESI) m/z calcd. for $C_{13}H_{20}NO_4S$ [M+H]⁺: 286.1108. found: 286.1113.

Preparation Example 4

Preparation of N-(2,2-dimethyl-1,3-dioxolane-4-ylmethyl)trifluoroacetamide in the Present Disclosure Under ice bath conditions, 5 mmol of (2,2-dimethyl-[1,3]-dioxolane-4-yl)-methylamine and 15 mmol of triethylamine were mixed in a dichloromethane solution, and stirred, and then 5 mol of trifluoroacetyl chloride was slowly dropwise added thereto for a reaction. The reaction was detected by TCL. After the reaction completed, water was added into the reaction product, obtaining an aqueous phase and an organic phase. The aqueous phase was extracted twice with dichloromethane. The organic phase was combined, and washed once with saturated brine, and separated, obtaining a separated organic phase. The separated organic phase was dried with anhydrous sodium sulfate and concentrated, obtaining N-(2,2-dimethyl-1,3-dioxolane-4-ylmethyl)trifluoroacetamide. The product is a light yellow liquid with a yield of 92%. The structural formula, and the experimental data of NMR and mass spectrometry of the product are shown as follows:

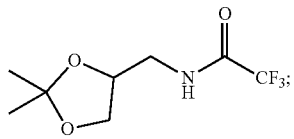

¹H NMR (400 MHz, CDCl₃) δ 6.69 (s, 1H), 4.52 (p, J=7.0 Hz, 1H), 3.96 (dd, J=11.4, 7.0 Hz, 1H), 3.80 (dd, J=12.4, 7.1 Hz, 1H), 3.71 (dd, J=11.5, 7.0 Hz, 1H), 3.46 (dd, J=12.4, 7.0 Hz, 1H), 1.39 (s, 3H), 1.34 (s, 3H).

¹³C NMR (100 MHz, CDCl₃) δ 159.2, 159.0, 158.7, 158.5, 118.7, 116.5, 114.4, 112.2, 109.4, 74.6, 67.0, 43.1, 43.1, 43.1, 25.5.

HRMS (ESI) m/z calcd. for $C_8H_{13}F_3NO_3$ [M+H]⁺: 228.0842. found: 228.088.

Preparation Example 5

Preparation of N-(2,2-dimethyl-1,3-dioxolane-4-ylmethyl)-N-ethynyl methanesulfonamide N-(2,2-dimethyl-1,3-dioxolane-4-ylmethyl)methanesulfonamide and 3 times the amount of 1,1-dichloroethylene were mixed in an organic solvent, and an alkali equal to times the molar amount of N-(2,2-dimethyl-1,3-dioxolane-4-ylmethyl)methanesulfonamide was added thereto for a reaction at a temperature of 70° C. The reaction was detected by TLC. After the reaction completed, ice water was added into the reaction solution, The resulting reaction solution was extracted three times with ethyl acetate, obtaining an organic layer. The organic layer was concentrated, and separated by column chromatography, obtaining the pure N-(2,2-dimethyl-1,3-dioxolane-4-ylmethyl)-N-ethynyl methanesulfonamide. The product is a white solid with a yield of 95%. The following are the structural formula, and the experimental data of NMR and mass spectrometry of the product are shown as follows:

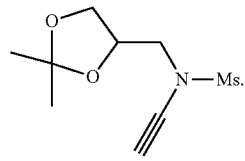

¹H NMR (400 MHz, DMSO) δ 4.33 (ddd, J=12.2, 6.8, 5.0 Hz, 1H), 4.05 (dd, J=8.7, 6.4 Hz, 1H), 3.86 (s, 1H), 3.73 (dd, J=8.7, 5.1 Hz, 1H), 3.49 (qd, J=14.1, 6.1 Hz, 2H), 3.25 (s, 3H), 1.36 (s, 3H), 1.28 (s, 3H).

$^{13}$C NMR (100 MHz, DMSO) δ 109.1, 75.9, 72.7, 66.0, 61.3, 53.5, 37.9, 26.6, 25.2.

HRMS (ESI) m/z calcd. for $C_9H_{16}NO_4S$ [M+H]$^+$: 234.0795. found: 234.0797.

Preparation Example 6

Preparation of N-(2,2-dimethyl-1,3-dioxolane-4-ylmethyl)-N-ethynyl benzenesulfonamide N-(2,2-dimethyl-1,3-dioxolane-4-ylmethyl)benzenesulfonamide and 3 times the amount of 1,1-dichloroethylene were mixed in an organic solvent, and an alkali equal to times the molar amount of N-(2,2-dimethyl-1,3-dioxolane-4-ylmethyl)benzenesulfonamide was added thereto for a reaction at a temperature of 70° C. The reaction was detected by TLC. After the reaction completed, ice water was added into the reaction solution, The resulting reaction solution was extracted three times with ethyl acetate, obtaining an organic layer. The organic layer was concentrated, and separated by column chromatography, obtaining the pure N-(2,2-dimethyl-1,3-dioxolane-4-ylmethyl)-N-ethynyl benzenesulfonamide. The product is a white solid with a yield of 94%. The following are the structural formula, and the experimental data of NMR and mass spectrometry of the product are shown as follows:

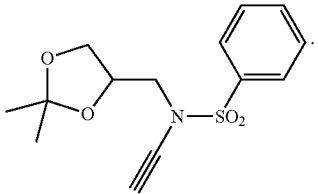 [SMILES: C#CN(CC1COC(C)(C)O1)S(=O)(=O)c1ccccc1]

$^1$H NMR (500 MHz, Chloroform-d) δ 7.86 (d, J=7.6 Hz, 2H), 7.62 (t, J=7.5 Hz, 1H), 7.52 (t, J=7.4 Hz, 2H), 4.41-4.30 (m, 1H), 4.10 (dd, J=8.8, 6.1 Hz, 1H), 3.89 (dd, J=8.8, 5.2 Hz, 1H), 3.53 (dd, J=13.4, 5.4 Hz, 1H), 3.30 (dd, J=13.4, 7.2 Hz, 1H), 2.73 (s, 1H), 2.44 (s, 3H), 1.40 (s, 3H), 1.32 (s, 3H).

$^{13}$C NMR (100 MHz, CDCl$_3$) δ 138.1, 133.8, 129.1, 127.9, 109.9, 76.4, 73.5, 67.4, 59.2, 53.7, 27.0, 25.4.

HRMS (ESI) m/z calcd. for $C_{14}H_{17}NNaO_4S$ [M+H]$^+$: 318.0770. found: 318.0778.

Preparation Example 7

Preparation of N-(2,2-dimethyl-1,3-dioxolane-4-ylmethyl)-N-ethynyl p-toluenesulfonamide N-(2,2-dimethyl-1,3-dioxolane-4-ylmethyl) p-toluenesulfonamide and 3 times the amount of 1,1-dichloroethylene were mixed in an organic solvent, and an alkali equal to times the molar amount of N-(2,2-dimethyl-1,3-dioxolane-4-ylmethyl)p-toluenesulfonamide was added thereto for a reaction at a temperature of 70° C. The reaction was detected by TLC. After the reaction completed, ice water was added into the reaction solution, The resulting reaction solution was extracted three times with ethyl acetate, obtaining an organic layer. The organic layer was concentrated, and separated by column chromatography, obtaining the pure N-(2,2-dimethyl-1,3-dioxolane-4-ylmethyl)-N-ethynyl p-toluenesulfonamide. The product is a white solid with a yield of 93%. The following are the structural formula, and the experimental data of NMR and mass spectrometry of the product are shown as follows:

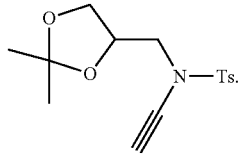 [SMILES: C#CN(CC1COC(C)(C)O1)S(=O)(=O)c1ccc(C)cc1]

$^1$H NMR (400 MHz, CDCl$_3$) δ 7.81 (d, J=8.3 Hz, 2H), 7.36 (d, J=8.0 Hz, 2H), 4.40-4.31 (m, 1H), 4.09 (dd, J=8.8, 6.1 Hz, 1H), 3.87 (dd, J=8.8, 5.2 Hz, 1H), 3.51 (dd, J=13.4, 5.4 Hz, 1H), 3.32 (dd, J=13.4, 7.2 Hz, 1H), 2.75 (s, 1H), 2.46 (s, 3H), 1.41 (s, 3H), 1.33 (s, 3H).

$^{13}$C NMR (100 MHz, CDCl$_3$) δ 145.1, 134.4, 130.0, 127.9, 109.9, 76.4, 73.5, 67.4, 59.2, 53.7, 27.0, 25.4, 21.8.

HRMS (ESI) m/z calcd. for $C_{15}H_{20}NO_4S$ [M+H]$^+$: 310.1108. found: 310.1116.

Preparation Example 8

Preparation of N-(2,2-dimethyl-1,3-dioxolane-4-ylmethyl)-N-ethynyl trifluoroacetamide N-(2,2-dimethyl-1,3-dioxolane-4-ylmethyl) p-toluenesulfonamide and 3 times the amount of 1,1-dichloroethylene were mixed in an organic solvent, and an alkali equal to times the molar amount of N-(2,2-dimethyl-1,3-dioxolane-4-ylmethyl)trifluoroacetamide was added thereto for a reaction at a temperature of 70° C. The reaction was detected by TLC. After the reaction completed, ice water was added into the reaction solution, The resulting reaction solution was extracted three times with ethyl acetate, obtaining an organic layer. The organic layer was concentrated, and separated by column chromatography, obtaining the pure N-(2,2-dimethyl-1,3-dioxolane-4-ylmethyl)-N-ethynyl trifluoroacetamide. The product is a light yellow liquid with a yield of 90%. The following are the structural formula, and the experimental data of NMR and mass spectrometry of the product are shown as follows:

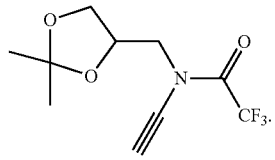 [SMILES: C#CN(CC1COC(C)(C)O1)C(=O)C(F)(F)F]

$^1$H NMR (400 MHz, CDCl$_3$) δ 4.52 (p, J=7.0 Hz, 1H), 3.96 (dd, J=11.4, 7.0 Hz, 1H), 3.71 (dd, J=11.5, 7.0 Hz, 1H), 3.44 (dd, J=12.4, 7.0 Hz, 1H), 3.19 (dd, J=12.4, 7.0 Hz, 1H), 2.45 (s, 1H), 1.39 (s, 3H), 1.34 (s, 3H).

$^{13}$C NMR (100 MHz, CDCl$_3$) δ 160.98, 160.72, 160.47, 160.21, 117.71, 115.57, 113.43, 111.29, 109.38, 77.87, 77.84, 77.81, 77.78, 74.09, 66.98, 57.51, 45.46, 45.45, 45.43, 25.55.

HRMS (ESI) m/z calcd. for $C_{10}H_{12}F_3NNaO_3$ [M+H]$^+$: 274.0661. found: 274.0657.

Application Example 1

Phenylpropionic acid (0.5 mmol) and N-(2,2-dimethyl-1,3-dioxolane-4-ylmethyl)-N-ethynyl methanesulfonamide (0.55 mmol) were dissolved in 3 mL of dichloromethane, and stirred for a reaction at room temperature. The process of the reaction was monitored by TLC. After phenylpropynoic acid consumed completely, 2-hydroxyethylamine (0.55 mmol) was added thereto. The process of the reaction was monitored by TLC. After the reaction completed, 15 mL of ethyl acetate was added to dilute the reaction solution, obtaining an organic phase. The organic phase was shaken and washed twice with 15 mL of 0.5 M dilute hydrochloric acid, and separated to remove the aqueous phase, obtaining a separated organic phase. The separated organic phase was dried with anhydrous magnesium sulfate, and subjected to a reduced pressure distillation to remove the solvent, obtaining a pure product. The product is a white solid with a yield of 90%. The structural formula, and the experimental data of NMR and mass spectrometry of the product were shown as follows:

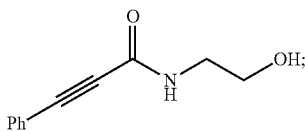 [SMILES: O=C(C#Cc1ccccc1)NCCO]

$^1$H NMR (400 MHz, CDCl$_3$) δ 7.51 (d, J=7.0 Hz, 2H), 7.39 (d, J=7.3 Hz, 1H), 7.33 (t, J=7.4 Hz, 2H), 6.83 (t, J=5.9 Hz, 1H), 3.80-3.75 (m, 2H), 3.52 (q, J=5.4 Hz, 2H).

$^{13}$C NMR (100 MHz, CDCl$_3$) δ 154.5, 132.6, 130.3, 128.6, 120.2, 85.6, 82.9, 61.5, 42.7.

HRMS (ESI) m/z calcd. for C$_{12}$H$_{12}$O$_2$ [M+H]$^+$:190.0868. found: 190.0867.

Application Example 2

Phenylpropionic acid (0.5 mmol) and N-(2,2-dimethyl-1,3-dioxolane-4-ylmethyl)-N-ethynyl methanesulfonamide (0.55 mmol) were dissolved in 3 mL of dichloromethane, and stirred for a reaction at room temperature. The process of the reaction was monitored by TLC. After the raw acid consumed completely, piperidine (0.55 mmol) was added thereto. The process of the reaction was monitored by TLC. After the reaction completed, 15 mL of ethyl acetate was added to dilute the reaction solution, obtaining an organic phase. The organic phase was shaken and washed twice with 15 mL of 0.5 M dilute hydrochloric acid, and separated to remove the aqueous phase, obtaining a separated organic phase. The separated organic phase was dried with anhydrous magnesium sulfate, and subjected to a reduced pressure distillation to remove the solvent, obtaining a pure product. The product is a white solid with a yield of 96%. The structural formula, and the experimental data of NMR and mass spectrometry of the product were shown as follows:

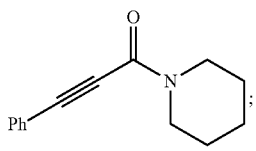 [SMILES: O=C(C#Cc1ccccc1)N1CCCCC1]

$^1$H NMR (400 MHz, CDCl$_3$) δ 7.54 (d, J=8.1 Hz, 2H), 7.43-7.33 (m, 3H), 3.80-3.75 (m, 2H), 3.65-3.59 (m, 2H), 1.71-1.64 (m, 4H), 1.62-1.56 (m, 2H).

$^{13}$C NMR (100 MHz, CDCl$_3$) δ 153.05, 132.41, 129.95, 128.57, 120.85, 90.37, 81.59, 48.33, 42.49, 26.56, 25.50, 24.65.

HRMS (ESI) m/z calcd. for C$_{14}$H$_{16}$NO [M+H]$^+$: 214.1226. found: 214.1230.

Application Example 3

Methyl benzoic acid (0.5 mmol) and N-(2,2-dimethyl-1,3-dioxolane-4-ylmethyl)-N-ethynyl methanesulfonamide (0.55 mmol) were dissolved in 3 mL of dichloromethane, and stirred for a reaction at room temperature. The process of the reaction was monitored by TLC. After the raw acid consumed completely, tetrahydropyrrole (0.55 mmol) was added thereto. The process of the reaction was monitored by TLC. After the reaction completed, the resulting reaction solution was subjected to a reduced pressure distillation to remove the solvent, a small amount of ethanol and 10 mL of 0.5 M dilute hydrochloric acid were added thereto, and stirred for 10 min, precipitating an product. The product was filtered, washed with water, obtaining a solid. The solid was collected, obtaining a pure product. The product is a white solid with a yield of 96%. The structural formula, and the experimental data of NMR and mass spectrometry of the product were shown as follows:

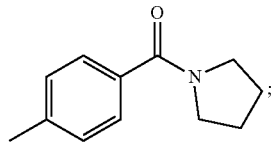

$^1$H NMR (400 MHz, CDCl$_3$) δ 7.42 (d, J=8.0 Hz, 2H), 7.19 (d, J=7.8 Hz, 2H), 3.64 (t, J=6.7 Hz, 2H), 3.44 (t, J=6.3 Hz, 2H), 2.37 (s, 3H), 1.94 (q, J=6.2 Hz, 2H), 1.87 (q, J=6.1 Hz, 2H).

$^{13}$C NMR (100 MHz, CDCl$_3$) δ 169.95, 139.98, 134.40, 128.90, 127.30, 49.75, 46.30, 26.51, 24.55, 21.46.

HRMS (ESI) m/z calcd. for C$_{12}$H$_{16}$NO [M+H]$^+$: 190.1226. found: 190.1225.

Application Example 4

Fmoc-Ala-OH (0.5 mmol) and N-(2,2-dimethyl-1,3-dioxolane-4-ylmethyl)-N-ethynyl methanesulfonamide (0.55 mmol) were dissolved in 5 mL of dichloromethane, and stirred for a reaction at room temperature. The process of the reaction was monitored by TLC. After the raw acid consumed completely, H-Phe-OtBu (0.55 mmol) was added thereto. The process of the reaction was monitored by TLC. After the reaction completed, 15 mL of ethyl acetate was added to dilute the reaction solution, obtaining an organic phase. The organic phase was shaken and washed twice with 15 mL of 0.2 M dilute hydrochloric acid, and separated to remove the aqueous phase, obtaining a separated organic phase. The separated organic phase was dried with anhydrous magnesium sulfate, and concentrated and then recrystallized with dichloromethane/petroleum ether, obtaining a pure product. The product is a white solid with a yield of 87%. The structural formula, and the experimental data of NMR and mass spectrometry of the product were shown as follows:

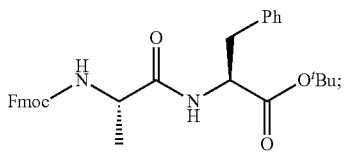

$^1$H NMR (400 MHz, CDCl$_3$) δ 7.75 (d, J=7.5 Hz, 2H), 7.58 (d, J=7.0 Hz, 2H), 7.38 (t, J=7.4 Hz, 2H), 7.29 (t, J=7.4 Hz, 2H), 7.24-7.10 (m, 5H), 6.69-6.48 (m, 1H), 5.60-5.40 (m, 1H), 4.73 (q, J=6.1 Hz, 1H), 4.39 (dd, J=10.3, 7.3 Hz, 1H), 4.36-4.22 (m, 2H), 4.19 (t, J=7.0 Hz, 1H), 3.08 (h, J=8.0, 7.2 Hz, 2H), 1.38 (s, 9H), 1.35 (s, 3H).

$^{13}$C NMR (100 MHz, CDCl$_3$) δ 171.84, 170.35, 155.94, 143.92, 141.37, 136.09, 129.56, 128.44, 127.80, 127.16, 127.05, 125.17, 120.06, 82.51, 67.20, 53.74, 50.51, 47.21, 38.07, 28.02, 18.87.

HRMS (ESI) m/z calcd. for C$_{31}$H$_{35}$N$_2$O$_5$[M+H]$^+$: 515.2540. found: 515.2547. dr>99:1.

Application Example 5

Fmoc-Aib-OH (0.5 mmol) and N-(2,2-dimethyl-1,3-dioxolane-4-ylmethyl)-N-ethynyl methanesulfonamide (0.55 mmol) were dissolved in 5 mL of dichloromethane, and stirred for a reaction at room temperature. The process of the reaction was monitored by TLC. After the raw acid consumed completely, H-Ala-OtBu (0.55 mmol) was added thereto. The process of the reaction was monitored by TLC. After the reaction completed, the resulting reaction solution was subjected to a reduced pressure distillation to remove the solvent, and a small amount of ethanol and 20 mL of 0.2 M dilute hydrochloric acid were added thereto, and stirred for 10 min, precipitating an product. The product was filtered, washed with water, obtaining a solid. The solid was collected, obtaining a pure product. The product is a white solid with a yield of 85%. The structural formula, and the experimental data of NMR and mass spectrometry of the product were shown as follows:

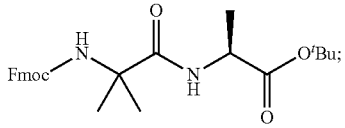

$^1$H NMR (400 MHz, CDCl$_3$) δ 7.75 (d, J=7.5 Hz, 2H), 7.61-7.57 (m, 2H), 7.39 (t, J=7.4 Hz, 2H), 7.31 (t, J=7.4 Hz, 2H), 6.74 (s, 1H), 5.52 (s, 1H), 4.45-4.35 (m, 3H), 4.20 (t, J=6.7 Hz, 1H), 1.53 (s, 6H), 1.44 (s, 9H), 1.35 (d, J=6.9 Hz, 3H).

$^{13}$C NMR (100 MHz, CDCl$_3$) δ 173.82, 172.23, 155.11, 144.00, 143.96, 141.42, 127.78, 127.17, 125.15, 125.12, 120.06, 82.13, 66.72, 56.84, 49.02, 47.33, 28.06, 25.71, 25.27, 18.54.

HRMS (ESI) m/z calcd. for C$_{26}$H$_{33}$N$_2$O$_5$[M+H]$^+$: 453,2384. found: 453.2380.

Application Example 6

Phenylpropionic acid (0.5 mmol) and N-(2,2-dimethyl-1,3-dioxolane-4-ylmethyl)-N-ethynyl methanesulfonamide (0.55 mmol) were dissolved in 3 mL of dichloromethane, and stirred for a reaction at room temperature. The process of the reaction was monitored by TLC. After the raw acid consumed completely, the resulting reaction solution was subjected to a reduced pressure distillation to remove dichloromethane, and 3 mL of acetonitrile was added thereto as a solvent, and 2-naphthol (0.55 mmol) and triethylamine (0.05 mmol) were added thereto. The process of the reaction was monitored by TLC. After the reaction completed, 10 mL of 0.5 M dilute hydrochloric acid was added the reaction system, and stirred for 10 min, precipitating an product. The product was filtered, washed with water, obtaining a solid. The solid was collected, obtaining a pure product. The product is a white solid with a yield of 96%. The structural formula, and the experimental data of NMR and mass spectrometry of the product were shown as follows:

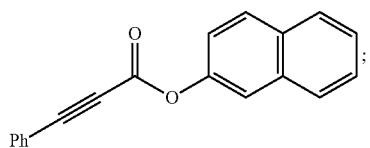 [SMILES: O=C(C#Cc1ccccc1)Oc1ccc2ccccc2c1]

$^1$H NMR (400 MHz, CDCl$_3$) δ 7.84 (dd, J=20.9, 9.9 Hz, 3H), 7.70-7.58 (m, 3H), 7.48 (dt, J=14.2, 7.4 Hz, 3H), 7.38 (t, J=7.5 Hz, 2H), 7.32 (d, J=8.8 Hz, 1H).

$^{13}$C NMR (100 MHz, CDCl$_3$) δ 152.57, 147.92, 133.81, 133.31, 131.81, 131.17, 129.74, 128.79, 127.92, 127.89, 126.86, 126.14, 120.84, 119.39, 118.74, 88.95, 80.46.

HRMS (ESI) m/z calcd. for C$_{19}$H$_{13}$O$_2$[M+H]$^+$: 273.0910. found: 273.0915.

Application Example 7

Quinoline-2-formic acid (0.5 mmol) and N-(2,2-dimethyl-1,3-dioxolane-4-ylmethyl)-N-ethynyl methanesulfonamide (0.55 mmol) were dissolved in 3 mL of dichloromethane, and stirred for a reaction at room temperature. The process of the reaction was monitored by TLC. After the raw acid consumed completely, the resulting reaction solution was subjected to a reduced pressure distillation to remove dichloromethane, and 3 mL of acetonitrile was added thereto as a solvent, and n-propanol (2.5 mmol) and triethylamine (0.2 mmol) were added thereto. The process of the reaction was monitored by TLC. After the reaction completed, 15 mL of ethyl acetate was added to dilute the reaction solution, obtaining an organic phase. The organic phase was shaken and washed twice with 15 mL of 0.5 M dilute hydrochloric acid, and separated to remove the aqueous phase, obtaining a separated organic phase. The separated organic phase was dried with anhydrous magnesium sulfate, and subjected to a reduced pressure distillation to remove the solvent, obtaining a pure product. The product is a light yellow solid with a yield of 93%. The structural formula, and the experimental data of NMR and mass spectrometry of the product were shown as follows:

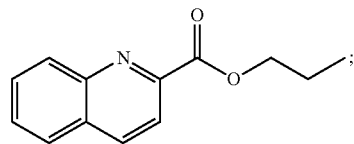 [SMILES: CCCOC(=O)c1ccc2ccccc2n1]

$^1$H NMR (400 MHz, CDCl$_3$) δ 8.31 (dd, J=10.3, 8.9 Hz, 2H), 8.17 (d, J=8.5 Hz, 1H), 7.87 (d, J=8.2 Hz, 1H), 7.78

(ddd, J=8.4, 6.9, 1.4 Hz, 1H), 7.64 (ddd, J=8.0, 7.0, 1.1 Hz, 1H), 4.46 (t, J=6.9 Hz, 2H), 1.94-1.86 (m, 2H), 1.06 (t, J=7.4 Hz, 3H).

$^{13}$C NMR (100 MHz, CDCl$_3$) δ 165.52, 148.40, 147.77, 137.28, 130.92, 130.27, 129.38, 128.61, 127.59, 121.10, 67.78, 22.21, 10.49.

HRMS (ESI) m/z calcd. for C$_{13}$H$_{14}$NO$_2$[M+H]$^+$: 216.1019. found: 216.1024.

Application Example 8

Cbz-Phe-OH (0.5 mmol) and N-(2,2-dimethyl-1,3-dioxolane-4-ylmethyl)-N-ethynyl methanesulfonamide (0.55 mmol) were dissolved in 3 mL of dichloromethane, and stirred for a reaction at room temperature. The process of the reaction was monitored by TLC. After the raw acid consumed completely, the resulting reaction solution was subjected to a reduced pressure distillation to remove dichloromethane, and 3 mL of acetonitrile was added thereto as a solvent, and 4-methoxyphenol (0.55 mmol) and N,N-diisopropylethylamine (0.05 mmol) were added thereto. The process of the reaction was monitored by TLC. 10 mL of 0.5 M dilute hydrochloric acid was added the reaction system, and stirred for 10 min, precipitating an product. The product was filtered, washed with water, obtaining a solid. The solid was collected, obtaining a pure product. The product is a white solid with a yield of 94%. The structural formula, and the experimental data of NMR and mass spectrometry of the product were shown as follows:

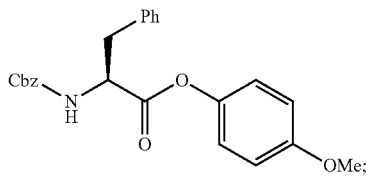 [SMILES: COc1ccc(OC(=O)[C@H](Cc2ccccc2)NC(=O)OCc2ccccc2)cc1]

$^1$H NMR (400 MHz, CDCl$_3$) δ 7.33-7.19 (m, 10H), 6.91-6.81 (m, 4H), 5.38 (s, 1H), 5.11 (s, 2H), 4.87 (q, J=5.7 Hz, 1H), 3.76 (s, 3H), 3.23 (d, J=5.7 Hz, 2H).

$^{13}$C NMR (100 MHz, CDCl$_3$) δ 170.63, 157.55, 155.78, 143.85, 136.28, 135.61, 129.53, 128.81, 128.62, 128.29, 128.18, 127.40, 122.08, 114.56, 67.16, 55.65, 55.08, 38.37.

HRMS (ESI) m/z calcd. for C$_{24}$H$_{24}$NO$_5$[M+H]$^+$: 406.1649. found: 406.1653. ee>99%.

Application Example 9

P-nitrobenzoic acid (0.5 mmol) and N-(2,2-dimethyl-1,3-dioxolane-4-ylmethyl)-N-ethynyl methanesulfonamide (0.55 mmol) were dissolved in 3 mL of dichloromethane, and stirred for a reaction at room temperature. The process of the reaction was monitored by TLC. After the raw acid consumed completely, the resulting reaction solution was subjected to a reduced pressure distillation to remove dichloromethane, and 3 mL of acetonitrile was added thereto as a solvent, and benzyl mercaptan (0.55 mmol) and N,N-diisopropylethylamine (0.05 mmol) were added thereto. The process of the reaction was monitored by TLC. 10 mL of 0.5 M dilute hydrochloric acid was added the reaction system, and stirred for 10 min, precipitating an product. The product was filtered, washed with water, obtaining a solid. The solid was collected, obtaining a pure product. The product is a white solid with a yield of 90%. The structural formula, and the experimental data of NMR and mass spectrometry of the product were shown as follows:

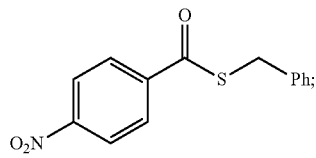 [SMILES: O=C(SCc1ccccc1)c1ccc([N+](=O)[O-])cc1]

$^1$H NMR (400 MHz, CDCl$_3$) δ 8.28 (d, J=8.9 Hz, 2H), 8.10 (d, J=8.9 Hz, 2H), 7.32 (ddt, J=22.8, 14.6, 7.4 Hz, 5H), 4.36 (s, 2H).

$^{13}$C NMR (100 MHz, CDCl$_3$) δ 189.89, 150.69, 141.52, 136.72, 129.12, 128.91, 128.42, 127.79, 124.01, 34.02.

HRMS (ESI) m/z calcd. for C$_{14}$H$_{12}$NO$_3$S[M+H]$^+$: 274.0532. found: 274.0538.

Application Example 10

Boc-Ala-OH (0.5 mmol) and N-(2,2-dimethyl-1,3-dioxolane-4-ylmethyl)-N-ethynyl methanesulfonamide (0.55 mmol) were dissolved in 3 mL of dichloromethane, and stirred for a reaction at room temperature. The process of the reaction was monitored by TLC. After the raw acid consumed completely, the resulting reaction solution was subjected to a reduced pressure distillation to remove dichloromethane, and 3 mL of acetonitrile was added thereto as a solvent, and 2-naphthylthiophenol (0.55 mmol) and N,N-diisopropylethylamine (0.05 mmol) were added thereto. The process of the reaction was monitored by TLC. After the reaction completed, 20 mL of 0.2 M dilute hydrochloric acid was added the reaction system, and stirred for 10 min, precipitating an product. The product was filtered, washed with water, obtaining a solid. The solid was collected, obtaining a pure product. The product is a white solid with a yield of 94%. The structural formula, and the experimental data of NMR and mass spectrometry of the product were shown as follows:

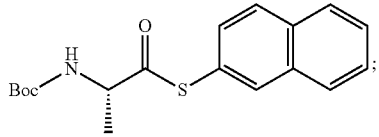 [SMILES: C[C@H](NC(=O)OC(C)(C)C)C(=O)Sc1ccc2ccccc2c1]

$^1$H NMR (400 MHz, CDCl$_3$) δ 7.94 (s, 1H), 7.87-7.79 (m, 3H), 7.54-7.47 (m, 2H), 7.43 (d, J=8.3 Hz, 1H), 5.10 (s, 1H), 4.65-4.43 (m, 1H), 1.50 (s, 9H), 1.46 (d, J=7.2 Hz, 3H).

$^{13}$C NMR (100 MHz, CDCl$_3$) δ 200.34, 155.08, 134.70, 133.70, 133.48, 131.10, 128.91, 128.04, 127.90, 127.25, 126.66, 124.75, 80.56, 56.47, 28.52, 18.83.

HRMS (ESI) m/z calcd. for C$_{18}$H$_{22}$NO$_3$S[M+H]$^+$: 332.1315. found: 332.1319. ee>99%.

Application Example 11

4-nitrobenzoic acid (0.5 mmol) and N-(2,2-dimethyl-1,3-dioxolane-4-ylmethyl)-N-ethynyl benzenesulfonamide (0.55 mmol) were dissolved in 3 mL of dichloromethane, and stirred for a reaction at room temperature. The process of the reaction was monitored by TLC. After the raw acid consumed completely, the resulting reaction solution was subjected to a reduced pressure distillation to remove dichloromethane, and 3 mL of acetonitrile was added thereto as a solvent, and trifluoroethanol (0.55 mmol) and triethylamine (0.05 mmol) were added thereto. The process of the reaction was monitored by TLC. After the reaction completed, 15 mL of ethyl acetate was added to dilute the reaction solution, obtaining an organic phase. The organic phase was shaken and washed twice with 15 mL of 0.5 M dilute hydrochloric acid, and separated to remove the aqueous phase, obtaining a separated organic phase. The separated organic phase was dried with anhydrous magnesium sulfate, and subjected to a reduced pressure distillation to remove the solvent, obtaining a pure product. The product is a white solid with a yield of 95%. The structural formula, and the experimental data of NMR and mass spectrometry of the product were shown as follows:

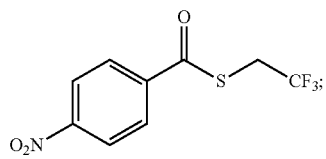 [SMILES: O=C(SCC(F)(F)F)c1ccc([N+](=O)[O-])cc1]

$^1$H NMR (400 MHz, CDCl$_3$) δ 8.34 (d, J=6.9 Hz, 2H), 8.26 (d, J=9.0 Hz, 2H), 4.76 (q, J=8.3 Hz, 2H).

$^{13}$C NMR (100 MHz, CDCl$_3$) δ 163.29, 151.25, 133.82, 131.32, 123.91, 62.10, 61.73, 61.36, 60.99.

HRMS (ESI) m/z calcd. for C$_9$H$_6$F$_3$NNaO$_4$ [M+Na]$^+$: 272.0141. found: 272.0135.

Application Example 12

Boc-Ala-OH (0.5 mmol) and N-(2,2-dimethyl-1,3-dioxolane-4-ylmethyl)-N-ethynyl benzenesulfonamide (0.55 mmol) were dissolved in 3 mL of dichloromethane, and stirred for a reaction at room temperature. The process of the reaction was monitored by TLC. After the raw acid consumed completely, the resulting reaction solution was subjected to a reduced pressure distillation to remove dichloromethane, and 3 mL of acetonitrile was added thereto as a solvent, and 2-naphthylthiophenol (0.55 mmol) and N,N-diisopropylethylamine (0.05 mmol) were added thereto. The process of the reaction was monitored by TLC. After the reaction completed, 20 mL of 0.2 M dilute hydrochloric acid was added the reaction system, and stirred for 10 min, precipitating an product. The product was filtered, washed with water, obtaining a solid. The solid was collected, obtaining a pure product. The product is a white solid with a yield of 94%. The structural formula, and the experimental data of NMR and mass spectrometry of the product were shown as follows:

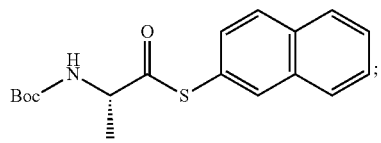 [SMILES: C[C@H](NC(=O)OC(C)(C)C)C(=O)Sc1ccc2ccccc2c1]

$^1$H NMR (400 MHz, CDCl$_3$) δ 7.94 (s, 1H), 7.87-7.79 (m, 3H), 7.54-7.47 (m, 2H), 7.43 (d, J=8.3 Hz, 1H), 5.10 (s, 1H), 4.65-4.43 (m, 1H), 1.50 (s, 9H), 1.46 (d, J=7.2 Hz, 3H).

$^{13}$C NMR (100 MHz, CDCl$_3$) δ 200.34, 155.08, 134.70, 133.70, 133.48, 131.10, 128.91, 128.04, 127.90, 127.25, 126.66, 124.75, 80.56, 56.47, 28.52, 18.83.

HRMS (ESI) m/z calcd. for C$_{18}$H$_{22}$NO$_3$S[M+H]$^+$: 332.1315. found: 332.1319. ee>99%.

Application Example 13

Pyridine-2-formic acid (0.5 mmol) and N-(2,2-dimethyl-1,3-dioxolane-4-ylmethyl)-N-ethynyl benzenesulfonamide (0.55 mmol) were dissolved in 3 mL of dichloromethane, and stirred for a reaction at room temperature. The process of the reaction was monitored by TLC. After the raw acid consumed completely, the resulting reaction solution was subjected to a reduced pressure distillation to remove dichloromethane, and tert-butylamine (0.55 mmol) was added thereto. The process of the reaction was monitored by TLC. After the reaction completed, 15 mL of ethyl acetate was added to dilute the reaction solution, obtaining an organic phase. The organic phase was shaken and washed twice with 15 mL of 0.5 M dilute hydrochloric acid, and separated to remove the aqueous phase, obtaining a separated organic phase. The separated organic phase was dried with anhydrous magnesium sulfate, and subjected to a reduced pressure distillation to remove the solvent, obtaining a pure product. The product is a white solid with a yield of 97%. The structural formula, and the experimental data of NMR and mass spectrometry of the product were shown as follows:

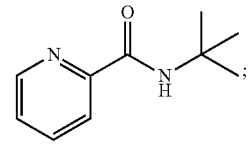

$^1$H NMR (400 MHz, CDCl$_3$) δ 8.52 (d, J=4.7 Hz, 1H), 8.18 (d, J=7.8 Hz, 1H), 8.01 (s, 1H), 7.83 (td, J=7.7, 1.5 Hz, 1H), 7.40 (dd, J=7.5, 4.8 Hz, 1H), 1.50 (s, 9H).

$^{13}$C NMR (100 MHz, CDCl$_3$) δ 163.56, 150.95, 147.87, 137.48, 125.96, 121.84, 51.05, 28.91.

HRMS (ESI) m/z calcd. for C10H14N2NaO [M+Na]$^+$: 201.0998. found: 201.1005.

Application Example 14

Cbz-Ala-OH (0.5 mmol) and N-(2,2-dimethyl-1,3-dioxolane-4-ylmethyl)-N-ethynyl benzenesulfonamide (0.55 mmol) were dissolved in 5 mL of dichloromethane, and stirred for a reaction at room temperature. The process of the reaction was monitored by TLC. After the raw acid consumed completely, H-Phe-OtBu (0.55 mmol) was added thereto. The process of the reaction was monitored by TLC. After the reaction completed, 15 mL of ethyl acetate was added to dilute the reaction solution, obtaining an organic phase. The organic phase was shaken and washed three times with 15 mL of 0.2 M dilute hydrochloric acid, and separated to remove the aqueous phase, obtaining a separated organic phase. The separated organic phase was dried with anhydrous magnesium sulfate, concentrated, and then recrystallized with dichloromethane/petroleum ether, obtaining a pure product. The product is a white solid with a yield of 93%. The structural formula, and the experimental data of NMR and mass spectrometry of the product were shown as follows:

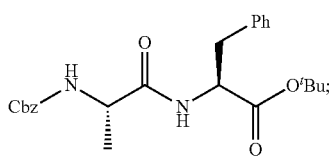

$^1$H NMR (400 MHz, CDCl$_3$) δ 7.38-7.28 (m, 5H), 7.26-7.19 (m, 3H), 7.13 (d, J=6.8 Hz, 2H), 6.69-6.45 (m, 1H), 5.51-5.34 (m, 1H), 5.10 (t, J=9.4 Hz, 2H), 4.72 (q, J=6.2 Hz, 1H), 4.34-4.16 (m, 1H), 3.11-3.03 (m, 2H), 1.40 (s, 9H), 1.33 (d, J=6.8 Hz, 3H).
$^{13}$C NMR (100 MHz, CDCl$_3$) δ 171.82, 170.36, 155.93, 136.35, 136.14, 129.60, 128.61, 128.45, 128.25, 128.12, 127.05, 82.52, 67.07, 53.72, 50.56, 38.06, 28.04, 18.69.
HRMS (ESI) m/z calcd. for C$_{24}$H$_{31}$N$_2$O$_5$ [M+H]$^+$: 427.2227. found: 427.2235. dr>99:1.

Application Example 15

Quinoline-2-formic acid (0.5 mmol) and N-(2,2-dimethyl-1,3-dioxolane-4-ylmethyl)-N-ethynyl p-toluenesulfonamide (0.55 mmol) were dissolved in 3 mL of dichloromethane, and stirred for a reaction at room temperature. The process of the reaction was monitored by TLC. After the raw acid consumed completely, the resulting reaction solution was subjected to a reduced pressure distillation to remove dichloromethane, and 3 mL of acetonitrile was added thereto as a solvent, and n-propanol (2.5 mmol) and triethylamine (0.2 mmol) were added thereto. The process of the reaction was monitored by TLC. After the reaction completed, 15 mL of ethyl acetate was added to dilute the reaction solution, obtaining an organic phase. The organic phase was shaken and washed twice with 15 mL of 0.5 M dilute hydrochloric acid, and separated to remove the aqueous phase, obtaining a separated organic phase. The separated organic phase was dried with anhydrous magnesium sulfate, and subjected to a reduced pressure distillation to remove the solvent, obtaining a pure product. The product is a light yellow solid with a yield of 91%. The structural formula, and the experimental data of NMR and mass spectrometry of the product were shown as follows:

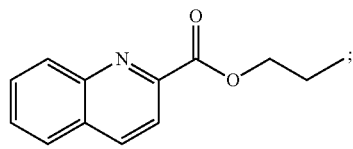 [SMILES: CCCOC(=O)c1ccc2ccccc2n1]

$^1$H NMR (400 MHz, CDCl$_3$) δ 8.31 (dd, J=10.3, 8.9 Hz, 2H), 8.17 (d, J=8.5 Hz, 1H), 7.87 (d, J=8.2 Hz, 1H), 7.78 (ddd, J=8.4, 6.9, 1.4 Hz, 1H), 7.64 (ddd, J=8.0, 7.0, 1.1 Hz, 1H), 4.46 (t, J=6.9 Hz, 2H), 1.94-1.86 (m, 2H), 1.06 (t, J=7.4 Hz, 3H).
$^{13}$C NMR (100 MHz, CDCl$_3$) δ 165.52, 148.40, 147.77, 137.28, 130.92, 130.27, 129.38, 128.61, 127.59, 121.10, 67.78, 22.21, 10.49.
HRMS (ESI) m/z calcd. for C$_{13}$H$_{14}$NO$_2$[M+H]$^+$: 216.1019. found: 216.1024.

Application Example 16

P-nitrobenzoic acid (0.5 mmol) and N-(2,2-dimethyl-1,3-dioxolane-4-ylmethyl)-N-ethynyl p-toluenesulfonamide (0.55 mmol) were dissolved in 3 mL of dichloromethane, and stirred for a reaction at room temperature. The process of the reaction was monitored by TLC. After the raw acid consumed completely, the resulting reaction solution was subjected to a reduced pressure distillation to remove dichloromethane, and 3 mL of acetonitrile was added thereto as a solvent, and benzyl mercaptan (0.55 mmol) and N,N-diisopropylethylamine (0.05 mmol) were added thereto. The process of the reaction was monitored by TLC. After the reaction completed, 10 mL of 0.5 M dilute hydrochloric acid was added the reaction system, and stirred for 10 min, precipitating an product. The product was filtered, washed with water, obtaining a solid. The solid was collected, obtaining a pure product. The product is a white solid with a yield of 88%. The structural formula, and the experimental data of NMR and mass spectrometry of the product were shown as follows:

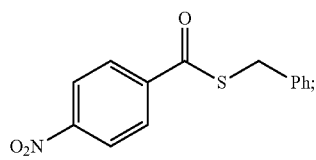 [SMILES: O=C(SCc1ccccc1)c1ccc([N+](=O)[O-])cc1]

$^1$H NMR (400 MHz, CDCl$_3$) δ 8.28 (d, J=8.9 Hz, 2H), 8.10 (d, J=8.9 Hz, 2H), 7.32 (ddt, J=22.8, 14.6, 7.4 Hz, 5H), 4.36 (s, 2H).
$^{13}$C NMR (100 MHz, CDCl$_3$) δ 189.89, 150.69, 141.52, 136.72, 129.12, 128.91, 128.42, 127.79, 124.01, 34.02.
HRMS (ESI) m/z calcd. for C$_{14}$H$_{12}$NO$_3$S[M+H]$^+$: 274.0532. found: 274.0538.

Application Example 17

Benzothiophene-2-formic acid (0.5 mmol) and N-(2,2-dimethyl-1,3-dioxolane-4-ylmethyl)-N-ethynyl p-toluenesulfonamide (0.55 mmol) were dissolved in 3 mL of dichloromethane, and stirred for a reaction at room temperature. The process of the reaction was monitored by TLC. After the phenylpropionic acid consumed completely, 2-hydroxyethylamine (0.55 mmol) was added thereto. The process of the reaction was monitored by TLC. After the reaction completed, 15 mL of ethyl acetate was added to dilute the reaction solution, obtaining an organic phase. The organic phase was shaken and washed twice with 15 mL of 0.5 M dilute hydrochloric acid, and separated to remove the aqueous phase, obtaining a separated organic phase. The separated organic phase was dried with anhydrous magnesium sulfate, and subjected to a reduced pressure distillation to remove the solvent, obtaining a pure product. The product is a white solid with a yield of 94%. The structural formula, and the experimental data of NMR and mass spectrometry of the product were shown as follows:

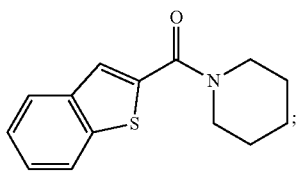 [SMILES: O=C(c1cc2ccccc2s1)N1CCCCC1]

¹H NMR (400 MHz, CDCl₃) δ 7.84 (dd, J=5.9, 3.2 Hz, 1H), 7.80 (dd, J=5.9, 3.2 Hz, 1H), 7.44 (s, 1H), 7.38 (dt, J=6.0, 3.5 Hz, 2H), 3.71-3.64 (m, 4H), 1.73-1.62 (m, 6H).

¹³C NMR (100 MHz, CDCl₃) δ=163.8, 140.2, 138.8, 137.4, 125.6, 124.8, 124.7, 124.6, 122.4, 26.3, 24.7.

HRMS (ESI) m/z calcd. for $C_{14}H_{16}NOS$ $[M+H]^+$: 246.0947. found: 246.0953.

Application Example 18

Boc-Ala-OH (0.5 mmol) and N-(2,2-dimethyl-1,3-dioxolane-4-ylmethyl)-N-ethynyl p-toluenesulfonamide (0.55 mmol) were dissolved in 5 mL of dichloromethane, and stirred for a reaction at room temperature. The process of the reaction was monitored by TLC. After the raw acid consumed completely, H-Phe-OtBu (0.55 mmol) was added thereto. The process of the reaction was monitored by TLC. After the reaction completed, 15 mL of ethyl acetate was added to dilute the reaction solution, obtaining an organic phase. The organic phase was shaken and washed three times with 15 mL of 0.2 M dilute hydrochloric acid, and separated to remove the aqueous phase, obtaining a separated organic phase. The separated organic phase was dried with anhydrous magnesium sulfate, concentrated, and then recrystallized with dichloromethane/petroleum ether, obtaining a pure product. The product is a white solid with a yield of 97%. The structural formula, and the experimental data of NMR and mass spectrometry of the product were shown as follows:

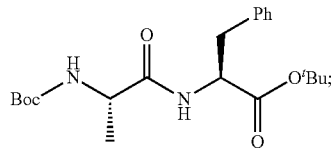 [SMILES: C[C@H](NC(=O)OC(C)(C)C)C(=O)N[C@@H](Cc1ccccc1)C(=O)OC(C)(C)C]

¹H NMR (400 MHz, CDCl₃) δ 7.25 (dt, J=13.1, 6.8 Hz, 3H), 7.15 (d, J=6.8 Hz, 2H), 6.60 (s, 1H), 5.05 (s, 1H), 4.71 (q, J=6.2 Hz, 1H), 4.15 (s, 1H), 3.13-3.04 (m, 2H), 1.43 (s, 9H), 1.39 (s, 9H), 1.32 (d, J=7.0 Hz, 3H).

¹³C NMR (100 MHz, CDCl₃) δ 172.23, 170.41, 155.40, 136.24, 129.64, 128.44, 127.02, 82.44, 80.13, 53.71, 50.28, 38.16, 28.40, 28.03, 18.55.

HRMS (ESI) m/z calcd. for $C_{22}H_{33}N_2O_5$ $[M+H]^+$: 393.2384. found: 393.2389. dr>99:1.

Application Example 19

Cbz-Gly-OH (0.5 mmol) and N-(2,2-dimethyl-1,3-dioxolane-4-ylmethyl)-N-ethynyl trifluoroacetamide (0.55 mmol) were dissolved in 3 mL of dichloromethane, and stirred for a reaction at room temperature. The process of the reaction was monitored by TLC. After the raw acid consumed completely, the resulting reaction solution was subjected to a reduced pressure distillation to remove dichloromethane, and 3 mL of acetonitrile was added thereto as a solvent, and estrone (0.55 mmol) and N,N-diisopropylethylamine (0.05 mmol) were added thereto. The process of the reaction was monitored by TLC. After the reaction completed, 20 mL of 0.2 M dilute hydrochloric acid was added the reaction system, and stirred for 10 min, precipitating an product. The product was filtered, washed with water, obtaining a solid. The solid was collected, obtaining a pure product. The product is a white solid with a yield of 90%. The structural formula, and the experimental data of NMR and mass spectrometry of the product were shown as follows:

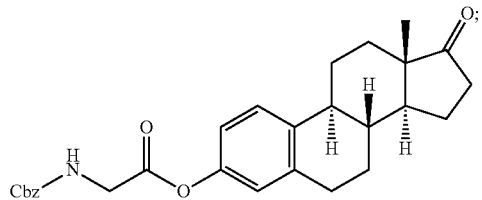

¹H NMR (400 MHz, CDCl₃) δ 7.38-7.25 (m, 6H), 6.91-6.72 (m, 2H), 5.46 (s, 1H), 5.14 (s, 2H), 4.20 (d, J=5.5 Hz, 2H), 2.94-2.84 (m, 2H), 2.50 (dd, J=18.9, 8.7 Hz, 1H), 2.42-2.34 (m, 1H), 2.30-2.22 (m, 1H), 2.18-1.94 (m, 4H), 1.65-1.41 (m, 6H), 0.90 (s, 3H).

¹³C NMR (100 MHz, CDCl₃) δ 168.95, 156.37, 148.18, 138.18, 137.80, 136.20, 128.56, 128.23, 128.10, 126.47, 121.28, 118.43, 67.21, 50.43, 47.93, 44.14, 42.99, 37.98, 35.84, 31.56, 29.38, 26.31, 25.76, 21.59, 13.83.

HRMS (ESI) m/z calcd. for $C_{28}H_{32}NO_5[M+H]^+$: 462.2275. found: 462.2281.

Application Example 20

Pyridine-2-formic (0.5 mmol) and N-(2,2-dimethyl-1,3-dioxolane-4-ylmethyl)-N-ethynyl trifluoroacetamide (0.55 mmol) were dissolved in 3 mL of dichloromethane, and stirred for a reaction at room temperature. The process of the reaction was monitored by TLC. After the raw acid consumed completely, the resulting reaction solution was subjected to a reduced pressure distillation to remove dichloromethane, and 3 mL of acetonitrile was added thereto as a solvent, and benzyl mercaptan (0.55 mmol) and triethylamine (0.05 mmol) were added thereto. The process of the reaction was monitored by TLC. 10 mL of 0.5 M dilute hydrochloric acid was added the reaction system, and stirred for 10 min, precipitating an product. The product was filtered, washed with water, obtaining a solid. The solid was collected, obtaining a pure product. The product is a white solid with a yield of 89%. The structural formula, and the experimental data of NMR and mass spectrometry of the product were shown as follows:

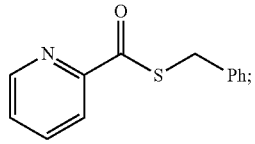 [SMILES: O=C(SCc1ccccc1)c1ccccn1]

¹H NMR (400 MHz, CDCl₃) δ 8.66 (d, J=4.7 Hz, 1H), 7.96 (d, J=7.8 Hz, 1H), 7.83 (td, J=7.7, 1.6 Hz, 1H), 7.50-7.46 (m, 1H), 7.39 (d, J=7.2 Hz, 2H), 7.29 (t, J=7.4 Hz, 2H), 7.26-7.21 (m, 1H), 4.28 (s, 2H).

¹³C NMR (100 MHz, CDCl₃) δ 193.07, 151.99, 149.23, 137.65, 137.31, 129.12, 128.66, 127.93, 127.28, 120.56, 33.29.

HRMS (ESI) m/z calcd. for $C_{13}H_{12}NOS$ $[M+H]^+$: 230.0634. found: 230.0640.

Application Example 21

Cinnamic acid (0.5 mmol) and N-(2,2-dimethyl-1,3-dioxolane-4-ylmethyl)-N-ethynyl trifluoroacetamide (0.55 mmol) were dissolved in 3 mL of dichloromethane, and stirred for a reaction at room temperature. The process of the reaction was monitored by TLC. After the raw acid consumed completely, 2-phenethylamine (0.55 mmol) was added thereto. The process of the reaction was monitored by TLC. After the reaction completed, 15 mL of ethyl acetate was added to dilute the reaction solution, obtaining an organic phase. The organic phase was shaken and washed twice with 15 mL of 0.5 M dilute hydrochloric acid, and separated to remove the aqueous phase, obtaining a separated organic phase. The separated organic phase was dried with anhydrous magnesium sulfate, and subjected to a reduced pressure distillation to remove the solvent, obtaining a pure product. The product is a white solid with a yield of 91%. The structural formula, and the experimental data of NMR and mass spectrometry of the product were shown as follows:

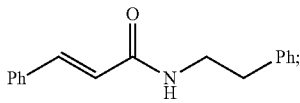 [SMILES: O=C(/C=C/c1ccccc1)NCCc1ccccc1]

$^1$H NMR (400 MHz, CDCl$_3$) δ 7.61 (d, J=15.6 Hz, 1H), 7.46 (dd, J=6.4, 2.5 Hz, 2H), 7.37-7.28 (m, 5H), 7.23 (t, J=9.5 Hz, 3H), 6.35 (d, J=15.6 Hz, 1H), 5.86 (s, 1H), 3.65 (q, J=6.8 Hz, 2H), 2.88 (t, J=6.9 Hz, 2H).
$^{13}$C NMR (100 MHz, CDCl$_3$) δ 166.04, 141.08, 139.00, 134.95, 129.74, 128.90, 128.89, 128.78, 127.88, 126.65, 120.83, 40.96, 35.80.
HRMS (ESI) m/z calcd. for C$_{17}$H$_{18}$NO [M+H]$^+$: 252.1383. found: 252.1390.

Application Example 22

Fmoc-Ser(tBu)-OH (0.5 mmol) and N-(2,2-dimethyl-1,3-dioxolane-4-ylmethyl)-N-ethynyl trifluoroacetamide (0.55 mmol) were dissolved in 5 mL of dichloromethane, and stirred for a reaction at room temperature. The process of the reaction was monitored by TLC. After the raw acid consumed completely, H-Leu-OtBu (0.55 mmol) was added thereto. The process of the reaction was monitored by TLC. After the reaction completed, 15 mL of ethyl acetate was added to dilute the reaction solution, obtaining an organic phase. The organic phase was shaken and washed three times with 15 mL of 0.2 M dilute hydrochloric acid, and separated to remove the aqueous phase, obtaining a separated organic phase. The separated organic phase was dried with anhydrous magnesium sulfate, concentrated, and then recrystallized with dichloromethane/petroleum ether, obtaining a pure product. The product is a white solid with a yield of 96%. The structural formula, and the experimental data of NMR and mass spectrometry of the product were shown as follows:

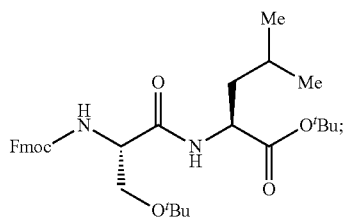

$^1$H NMR (400 MHz, CDCl$_3$) δ 7.75 (d, J=7.5 Hz, 2H), 7.60 (d, J=6.9 Hz, 2H), 7.39 (t, J=7.4 Hz, 2H), 7.30 (t, J=7.4 Hz, 2H), 7.22 (s, 1H), 5.80 (s, 1H), 4.49 (s, 1H), 4.42-4.36 (m, 2H), 4.23 (t, J=7.1 Hz, 2H), 3.83 (dd, J=8.3, 3.4 Hz, 1H), 3.40 (t, J=8.0 Hz, 1H), 1.76-1.59 (m, 3H), 1.58-1.47 (m, 3H), 1.45 (s, 9H), 1.22 (s, 9H), 0.95 (d, J=6.2 Hz, 6H).
$^{13}$C NMR (100 MHz, CDCl$_3$) δ 171.69, 169.99, 156.11, 143.98, 143.86, 141.36, 127.77, 127.14, 125.20, 120.03, 81.76, 74.31, 67.21, 61.89, 54.41, 51.74, 47.25, 41.96, 28.06, 27.43, 24.95, 22.90, 22.24.
HRMS (ESI) m/z calcd. for C$_{32}$H$_{45}$N$_2$O$_6$ [M+H]$^+$: 553.3272. found: 553.3279. dr>99:1.

The above examples are merely the description of the preferred embodiments of the present disclosure, and they should not be limited the scope of the present disclosure. Without departing from the design spirit of the present disclosure, various modifications and improvements made by those skilled in the art to the technical solutions of the present disclosure should be fall within the protection scope determined by the claims of the present disclosure.

What is claimed is:
1. A water-soluble ynamide coupling reagent, wherein the ynamide coupling reagent has the structure represented by the following formula (I):

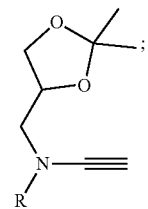

and
in the formula (I), R is selected from the group consisting of methylsulfonyl, benzenesulfonyl, p-toluenesulfonyl, trifluoroacetyl and other electron withdrawing groups.
2. A method for preparing the water-soluble ynamide coupling reagent of claim 1, comprising:
1) Mixing N-(2,2-dimethyl-1,3-dioxolane-4-ylmethyl) amide having the structure represented by formula (II) and ethylene dichloride in a solvent I to obtain a mixture;
2) Adding an alkali or DBU into the mixture obtained in step 1), and subjecting the resulting mixture to a reaction, and separating to obtain the water-soluble ynamide coupling reagent having the structure represented by formula (I); the specific reaction is performed as follows:

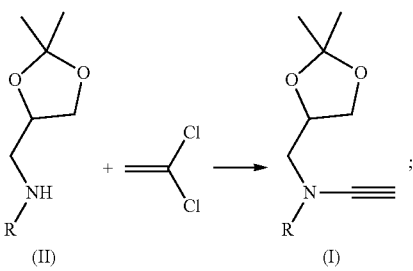

and
   wherein, R is selected from the group consisting of methylsulfonyl, benzenesulfonyl, p-toluenesulfonyl, trifluoroacetyl and other electron withdrawing groups.

3. The method of claim 2, wherein in step 1), the solvent I is an organic solvent; a molar ratio of N-(2,2-dimethyl-1,3-dioxolane-4-ylmethyl)amide having the structure represented by formula (II) to ethylene dichloride is in a range of 1:(0.8-5); and/or
   in step 2), the alkali is selected from the group consisting of NaH, CaH$_2$, t-BuONa, KOH, NaOH, EtONa, EtOLi, Cs$_2$CO$_3$, K$_2$CO$_3$, Na$_2$CO$_3$, Ca(OH)$_2$, and LiOH; the reaction is performed at a temperature of 15-100° C.; the reaction is performed for 0.2-48 h; the separating is performed by filtration, centrifugation or column chromatography; and a molar ratio of the alkali to N-(2,2-dimethyl-1,3-dioxolane-4-ylmethyl) amide having the structure represented by formula (II) is in a range of (1-10):1.

4. A method for using a water-soluble ynamide coupling reagent, wherein the water-soluble ynamide coupling reagent of claim 1 is used in the synthesis of an ester compound or a thioester compound, wherein the method for using the water-soluble ynamide coupling reagent to synthesize an ester compound or a thioester compound is performed as follows:

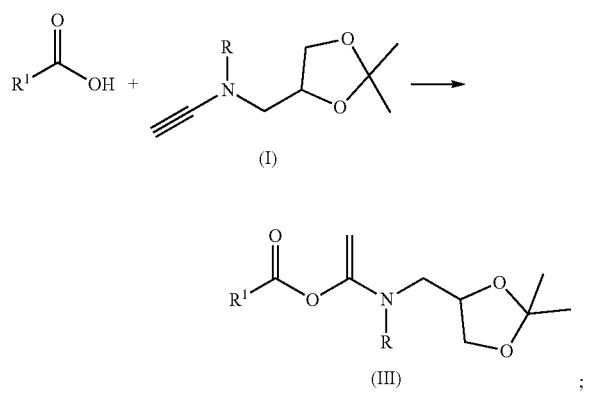

1a) subjecting a carboxylic acid compound and the water-soluble ynamide coupling reagent having the general molecular formula (I) to a reaction in a solvent II to obtain a compound having the structure represented by formula (III); the specific reaction is performed as follows:

2a) after the reaction in step 1a) is completed, dissolving the compound having the structure represented by formula (III) in a solvent III, adding a compound selected from the group consisting of an alcohol compound, an aromatic alcohol compound, a thiol compound and an aromatic thiol compound thereto, adding a catalyst thereto, and stirring for a reaction to obtain a mixture containing an ester compound or a thioester compound, and a by-product; the specific reaction is performed as follows:

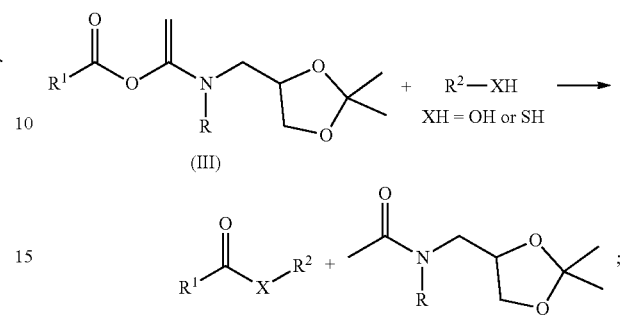

3a) after the reaction is completed, adding a dilute acid aqueous solution into the mixture containing an ester compound or a thioester compound obtained in step 2a), hydrolyzing unreacted coupling reagent from step 1a) and the by-product produced in the reaction, and separating to obtain the target ester compound or thioester compound; the reaction is performed as follows:

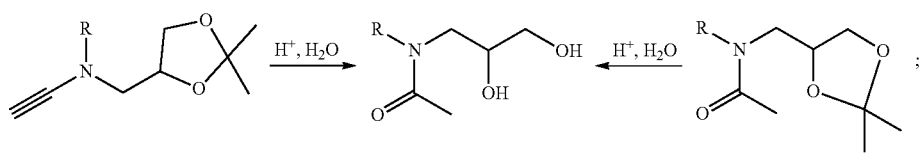

and
   in the formula, R$^1$ is selected from the group consisting of alkyl, cycloalkyl, alkenyl, alkynyl, aryl, heterocyclic, heterocyclic aryl, protected α-aminoalkyl, and protected β-aminoalkyl; R is selected from the group consisting of methylsulfonyl, benzenesulfonyl, p-toluenesulfonyl, trifluoroacetyl and other electron withdrawing groups; and R$^2$ is selected from the group consisting of aliphatic substituent group and aromatic substituent group.

5. The method of claim 4, wherein in step 1a), a molar ratio of the carboxylic acid compound to the water-soluble ynamide coupling reagent having the general molecular formula (I) is in a range of 1:(1-5); the solvent II is selected from the group consisting of dichloromethane, water, chloroform and 1,2-dichloroethane, or the solvent II is a mixture of water and dimethylsulfoxide, or a mixture of water and N,N-dimethylformamide; and/or
   in step 2a), a molar ratio of the alcohol compound, the aromatic alcohol compound, the thiol compound and the aromatic thiol compound to the carboxylic acid compound is in a range of 1:(1-20); the solvent III is selected from the group consisting of water, acetonitrile, dimethyl sulfoxide, N,N-dimethylformamide, N,N-dimethylacetamide, N-methylpyrrolidone, a mixture of acetonitrile and water, a mixture of water and dimethylsulfoxide, and a mixture of water and N,N-dimethylformamide; the catalyst is triethylamine or N,N-diisopropylethylamine; a molar ratio of the catalyst to the carboxylic acid compound is in a range of (0.01-10):1; and/or
   in step 3a), the dilute acid is selected from the group consisting of dilute sulfuric acid, dilute hydrochloric acid, phosphoric acid, acetic acid and citric acid; and the concentration of the dilute acid is in a range of 0.01-5 mol/L.

6. The method of claim 4, wherein the step 1a) is performed as follows: adding the carboxylic acid compound, the water-soluble ynamide coupling reagent having the general molecular formula (I) and the solvent II into a reactor for mixing, and stirring for a reaction at a temperature of 0-60° C., after the reaction is completed, removing the solvent II to obtain a compound having the structure represented by formula (III); and/or the step 2a) is performed as follows: after the reaction in step 1a) is completed, dissolving the compound having the structure represented by formula (III) obtained in step 1a) into the solvent III, adding one selected from the group consisting of alcohol compound, aromatic alcohol compound, thiol compound and aromatic thiol compound thereto, adding a catalyst thereto, and then stirring for a reaction at a temperature of 0-60° C. to obtain a mixture containing an ester compound or a thioester compound; and/or the step 3a) is performed as follows: optionally adding a diluent into the mixture containing an ester compound or a thioester compound obtained in step 2a) for dilution, and then adding a diluted acid aqueous solution for washing, hydrolyzing unreacted coupling reagent from step 1a) and the by-product produced in the reaction to precipitate a product, filtering the product, and washing with water to obtain the target ester compound or thioester compound.

7. A method for using a water-soluble ynamide coupling reagent, wherein the water-soluble ynamide coupling reagent of claim 1 is used in the synthesis of an amide, or a polypeptide, wherein the method for using the water-soluble ynamide coupling reagent to synthesize an amide compound or a polypeptide compound is performed as follows:

1b) subjecting a carboxylic acid compound and the water-soluble ynamide coupling reagent having the general molecular formula (I) to a reaction in a solvent II to obtain a compound having the structure represented by the formula (IV); the specific reaction is performed as follows:

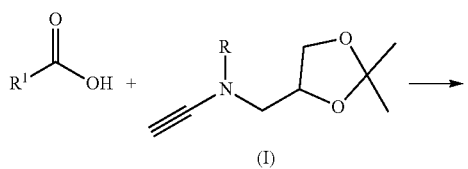

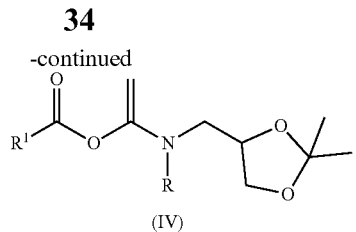

2b) after the reaction in step 1b) is completed, adding an amine compound to the obtained compound having the structure represented by formula (IV), and stirring for a reaction to obtain a mixture containing an amide compound or a polypeptide compound and a by-product; the specific reaction is performed as follows:

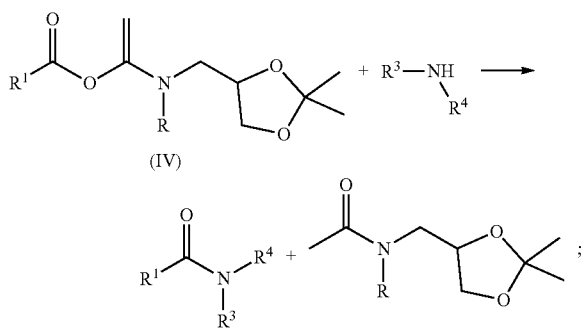

3b) adding a diluent and a diluted acid aqueous solution into the mixture containing an amide compound or a polypeptide compound and a by-product obtained in step 2b), hydrolyzing the unreacted coupling reagent and the by-product produced in the reaction, and separating to obtain the target amide compound or polypeptide compound; the reaction is performed as follows:

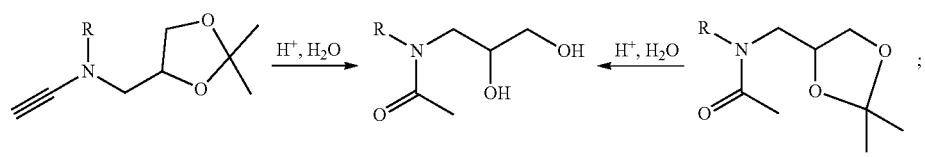

and in the formula, $R^1$ is selected from the group consisting of alkyl, cycloalkyl, alkenyl, alkynyl, aryl, heterocyclic, heterocyclic aryl, protected α-aminoalkyl, and protected β-aminoalkyl; R is selected from the group consisting of methylsulfonyl, benzenesulfonyl, p-toluenesulfonyl, trifluoroacetyl and other electron withdrawing groups; $R^3$ and $R^4$ are each selected from the group consisting of aliphatic substituent group and aromatic substituent group.

8. The method of claim 7, wherein in step 1b), a molar ratio of the carboxylic acid compound to the water-soluble ynamide coupling reagent having the general molecular formula (I) is in a range of 1:(1-5); the solvent II is an organic solvent; and/or in step 2b), a molar ratio of the compound having the structure represented by formula (IV) to the amine compound is in a range of 1:(1-5); and/or in step 3b), the dilute acid is selected from the group consisting of dilute sulfuric acid, dilute hydrochloric acid, phosphoric acid, acetic acid and citric acid; a concentration of the dilute acid is in a range of 0.01-5 mol/L.

9. The method of claim 7, wherein the step 1b) is performed as follows: adding the carboxylic acid compound, the water-soluble ynamide coupling reagent having the general molecular formula (I) and the solvent II into a reactor for mixing, and stirring for a reaction at a temperature of 0-60° C. to obtain a compound having a structure represented by formula (IV); and/or the step 2b) is performed as follows: after the reaction in step 1b) is completed, adding an amine compound to the compound having the structure represented by formula (IV) obtained in step 1b), and then stirring for a reaction at a temperature of 0-60° C. to obtain a mixture containing an amide compound or a polypeptide compound and a by-product; and/or the step 3b) is performed as follows: adding a diluent into the mixture containing an amide compound or a polypeptide compound obtained in step 2b); and then adding a dilute acid aqueous solution for washing, hydrolyzing any unreacted coupling reagent of formula (I) and any by-product obtained in the reaction to precipitate a product, filtering the product, and washing with water to obtain the target amide compound or polypeptide compound; or the step 3b) is performed as follows: removing the solvent in the mixture containing an amide compound or a polypeptide compound obtained in step 2b), adding solvent IV, and then adding a dilute acid for washing, hydrolyzing the unreacted coupling reagent and the by-product obtained in the reaction to precipitate a product, filtering the product, and washing with water to obtain the target amide compound or polypeptide compound.

\* \* \* \* \*